(12) United States Patent
Yuan et al.

(10) Patent No.: US 7,037,922 B1
(45) Date of Patent: May 2, 2006

(54) ARYL FUSED 2,4-DISUBSTITUTED PYRIDINES: NK3 RECEPTOR LIGANDS

(75) Inventors: Jun Yuan, Guilford, CT (US); George Maynard, Clinton, CT (US); Alan Hutchison, Waterford, CT (US)

(73) Assignee: Neurogen Corporation, Branford, CT (US)

( * ) Notice: Subject to any disclaimer, the term of this patent is extended or adjusted under 35 U.S.C. 154(b) by 0 days.

(21) Appl. No.: 09/914,957

(22) PCT Filed: Mar. 10, 2000

(86) PCT No.: PCT/US00/06371

§ 371 (c)(1),
(2), (4) Date: Jan. 22, 2002

(87) PCT Pub. No.: WO00/58307

PCT Pub. Date: Oct. 5, 2000

(51) Int. Cl.
*C07D 471/04* (2006.01)
*A61K 31/435* (2006.01)

(52) U.S. Cl. ............... 514/300; 546/122; 546/123

(58) Field of Classification Search ............ 546/122, 546/123; 514/300
See application file for complete search history.

(56) References Cited

U.S. PATENT DOCUMENTS

| | | | |
|---|---|---|---|
| 5,811,553 | A | 9/1998 | Farina et al. |
| 6,277,862 | B1 | 8/2001 | Giardina et al. |
| 6,355,654 | B1 | 3/2002 | Giardina et al. |
| 6,432,977 | B1 | 8/2002 | Giardina et al. |
| 6,608,083 | B1 | 8/2003 | Farina et al. |
| 6,613,770 | B1 | 9/2003 | Farina et al. |
| 6,743,804 | B1 | 6/2004 | Giardina et al. |
| 6,780,875 | B1 | 8/2004 | Farina et al. |

FOREIGN PATENT DOCUMENTS

| | | | |
|---|---|---|---|
| DE | 829894 | * | 1/1952 |
| WO | WO 97/19926 | | 6/1997 |
| WO | 00/31037 | | 6/2000 |
| WO | 02/38547 | | 5/2002 |
| WO | 02/38548 | | 5/2002 |
| WO | 02/43734 | | 6/2002 |
| WO | 02/44154 | | 6/2002 |

OTHER PUBLICATIONS

Gao et al, Current Medicinal Chemistry, 1999, 6: 375-388.*
Giardina, et al., (1999) *IL FARMACO*, 54:364-374.

* cited by examiner

*Primary Examiner*—Zinna Northington Davis
(74) *Attorney, Agent, or Firm*—McDonnell Boehnen Hulbert & Berghoff LLP

(57) ABSTRACT

Disclosed are compounds of formula (I) or pharmaceutically acceptable non-toxic salts or pharmaceutically acceptable solvates thereof wherein: (II) represents (a), (b), (c) or (d) and W, X, Y, A, B, C, D, E are variables as described herein. These compounds are highly selective agonists or antagonists at NK3 receptors or prodrugs thereof. The novel tachykinin NK-3 receptor antagonists contained in this invention have potential utility in the treatment of a broad array of disorders and diseases of the central nervous system (CNS) and periphery in mammals in which activation of NK-3 receptors is of importance.

19 Claims, No Drawings

ARYL FUSED 2,4-DISUBSTITUTED PYRIDINES: NK3 RECEPTOR LIGANDS

This application is a 371 of PCT/US00/06371 filed Mar. 10, 2000.

BACKGROUND OF THE INVENTION

1. Field of the Invention

This invention relates to aryl fused 2,4-disubstituted pyridines that bind to cell surface receptors, particularly neurokinin-3 (NK-3) receptors. More specifically, the invention relates to such compounds that selectively bind to such receptors. This invention also relates to pharmaceutical compositions comprising such compounds. These novel NK-3 receptor ligands are useful in the treatment of a broad array of disorders and diseases of the central nervous system (CNS) and peripheral nervous systems in mammals that are associated with pathogenic NK-3 receptor activation.

2. Description of the Related Art

The tachykinins represent a family of structurally related peptides originally isolated based upon their smooth muscle contractile and sialogogic activity. These mammalian peptides include substance P (SP), neurokinin A (NKA) and neurokinin β (NKB). Tachykinins are synthesized in the central nervous system (CNS), as well as in peripheral tissues, where they exert a variety of biological activities. Substance P can be produced from three different mRNAs (α-, β- and γ-preprotachykinin mRNAs) that arise from a single gene as a result of alternative RNA splicing, whereas NKA can be generated from either the β- or the γ-preprotachykinin mRNA through posttranslationally processed precursor polypeptides. These precursors can also be differentially processed so that amino terminally extended forms of NKA (known as neuropeptide K and neuropeptide γ) are produced. NKB is produced from a separate mRNA arising from a second gene known as preprotachykinin B.

Three receptors for the tachykinin peptides have been molecularly characterized and are referred to as neurokinin-1 (NK-1), neurokinin-2 (NK-2) and neurokinin-3 (NK-3) receptors. The NK-1 receptor has a natural agonist potency profile of SP>NKA>NKB. The NK-2 receptor agonist potency profile is NKA>NKB>SP, and the NK-3 receptor agonist potency profile is NKB>NKA>SP. These receptors mediate the variety of tachykinin-stimulated biological effects that generally include 1) modulation of smooth muscle contractile activity, 2) transmission of (generally) excitatory neuronal signals in the CNS and periphery (e.g. pain signals), 3) modulation of immune and inflammatory responses, 4) induction of hypotensive effects via dilation of the peripheral vasculature, and 5) stimulation of endocrine and exocrine gland secretions. These receptors transduce intracellular signals via the activation of pertussis toxin-insensitive ($G_{\alpha q/11}$) G proteins, resulting in the generation of the intracellular second messengers inositol 1,4,5-trisphosphate and diacylglycerol. NK-1 receptors are expressed in a wide variety of peripheral tissues and in the CNS. NK-2 receptors are expressed primarily in the periphery, while NK-3 receptors are primarily (but not exclusively) expressed in the CNS. Recent work confirms the presence of NK-3 receptor binding sites in the human brain.

Studies measuring the localization of NKB and NK-3 receptor mRNAs and proteins, along with studies performed using peptide agonists and non-peptide NK-3 receptor antagonists, provide a rationale for using NK-3 receptor antagonists in treating a variety of disorders in both the CNS and the periphery. In the CNS, activation of NK-3 receptors has been shown to modulate dopamine and serotonin release, indicating therapeutic utility in the treatment of a variety of disorders including anxiety, depression, schizophrenia and obesity. Further, studies in primate brain detect the presence of NK-3 mRNA in a variety of regions relevant to these disorders. With regard to obesity, it has also been shown that NK-3 receptors are located on MCH-containing neurons in the rat lateral hypothalamus and zona incerta. In the periphery, administration of NKB into the airways is known to induce mucus secretion and bronchoconstriction, indicating therapeutic utility for NK-3 receptor antagonists in the treatment of patients suffering from airway diseases such as asthma and chronic obstructive pulmonary disease (COPD). Localization of NK-3 receptors in the gastrointestinal (GI) tract and the bladder indicates therapeutic utility for NK-3 receptor antagonists in the treatment of GI and bladder disorders including inflammatory bowel disease and urinary incontinence.

Both peptide and nonpeptide antagonists have been developed for each of the tachykinin receptors. The first generation of peptide antagonists for the tachykinin receptors had problems with low potency, partial agonism, poor metabolic stability and toxicity, whereas the current generation of non-peptide antagonists display more drug-like properties. Unfortunately, previous non-peptide NK-3 receptor antagonists suffer from a number of problems such as species selectivity (which limits the potential to evaluate these compounds in many appropriate disease models). New non-peptide NK-3 receptor antagonists are therefore being sought, both as therapeutic agents and as tools to further investigate the anatomical and ultrastructural distribution of NK-3 receptors, as well as the physiologic and pathophysiologic consequences of NK-3 receptor activation.

SUMMARY OF THE INVENTION

This invention provides novel compounds of Formula I (below), which interact with the NK3 binding site (the NK-3 receptor). The invention provides pharmaceutical compositions containing compounds described by Formula I. These novel tachykinin NK-3 receptor ligands act as receptor antagonists. As such, they useful in the treatment of a broad array of disorders and diseases of the central nervous system (CNS) and periphery in mammals in which pathogenic activation of NK-3 receptors may occur. These include anxiety, panic disorder, depression, psychosis, obsessive compulsive disorder, dementia, Huntington's disease, schizophrenia, stress related somatic disorders, reflex sympathetic dystrophy, dysthmic disorders, Parkinson's disease, movement disorders, obesity, eating disorders, addiction, convulsive disorders such as epilepsy, neurodegenerative diseases such as Alzheimer's disease, Multiple sclerosis and other demyelinating diseases, AIDS related neuropathy, chemotherapy-induced neuropathy and neuralgia, diabetic or peripheral neuropathy, neurogenic inflammation, inflammatory pain and other types of chronic or acute pain, migraine, Reynaud's disease, vasodilation, vasospasm, angina, asthma, chronic obstructive pulmonary diseases, airway hyperreactivity, cough, allergic rhinitis, bronchospasm, bronchopneumonia, ocular inflammation, inflammatory bowel disease, Crohn's disease, ulcerative colitis, skin disorders and itch, hypersensitivity disorders, atopic dermatitis, contact dermatitis, cutaneous wheal and flare, psoriasis, renal disorders, urinary incontinence, immune system disorders and adverse immunological reactions, fibrositis, osteoarthritis, eosinophilic fascioliasis, and scleroderma.

These compounds are also useful for the diagnosis of disorders involving activation of tachykinin NK-3 receptors and as probes for detecting NK-3 receptors in cultured cells and tissue samples.

Accordingly, a broad embodiment of the invention is directed to compounds of Formula I:

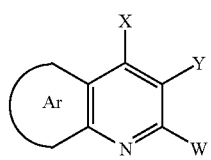

I and the pharmaceutically acceptable non-toxic salts or pharmaceutically acceptable solvates thereof wherein:

Y is
  hydrogen, straight or branched chain lower alkyl having 1–6 carbon atoms,
  halogen, amino, hydroxyl, or lower alkoxy having 1–6 carbon atoms; or
Y is
  straight or branched chain lower alkyl having 1–6 carbon atoms or lower alkoxy having 1–6 carbon atoms which is substituted on the alkyl chain with an amino or mono or dialkylamino group;
W is
  phenyl, thienyl, or pyridyl, each of which may be mono or disubstituted with halogen, cyano, trifluoromethyl, trifluoromethoxy, hydroxy, straight or branched chain lower alkyl having 1–6 carbon atoms, amino, mono or dialkylamino where each alkyl is straight or branched chain lower alkyl having 1–6 carbon atoms, or straight or branched chain lower alkoxy having 1–6 carbon atoms; or
W is
  straight or branched chain lower alkyl having 1–6 carbon atoms, cycloalkyl containing 5 to 8 carbon atoms or phenyl, thienyl or pyridyl straight or branched chain lower alkyl having 1–6 carbon atoms with all aryl groups being either unsubstituted or mono or disubstituted with halogen, cyano, trifluoromethyl, trifluoromethoxy, hydroxy, straight or branched chain lower alkyl having 1–6 carbon atoms, amino, mono or dialkylamino where each alkyl is straight or branched chain lower alkyl having 1–6 carbon atoms, or straight or branched chain lower alkoxy having 1–6 carbon atoms; or
W is
  piperidino, morpholino, thiomorpholino, pyrrolindino, piperazino, homopiperazino, azabicyclo[3.2.2]nonano, isoindolino, as well as any other nitrogen-containing heterocycle attached on nitrogen so as to form a tertiary amine in structure I wherein the heterocycle is unsubstituted, mono or disubstituted with alkyl or aryl groups, or fused to an aromatic ring; or
W is
  nitrogen that is mono or disubstituted with a hydrogen, a straight or branched alkyl chain consisting of 1 to 8 carbons, a cycloalkyl containing 3 to 8 carbon atoms, an alkyl chain having 1 to 6 carbon atoms that is attached at any position to an aryl ring, an alkyl chain having 1 to 6 carbon atoms that is attached at any position to a cycloalkyl containing 3 to 8 carbon atoms, phenyl, thienyl, pyridyl, imidazolyl, benzimidazolyl, or any heterocycle having aromatic character; or
W is
  oxygen that is substituted with a straight or branched alkyl chain having 1 to 8 carbon atoms, a cycloalkyl having 3 to 8 carbon atoms, or a phenyl ring that is mono or disubstituted with halogen, cyano, trifluoromethyl, trifluoromethoxy, hydroxy, straight or branched chain lower alkyl having 1–6 carbon atoms, amino, mono or dialkylamino where each alkyl is straight or branched chain lower alkyl having, 1–6 carbon atoms, or straight or branched chain lower alkoxy having 1–6 carbon atoms;

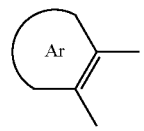

represents

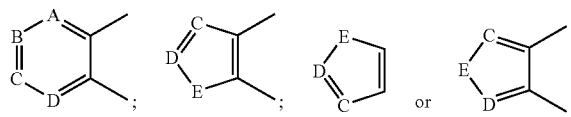

wherein:
  A represents nitrogen or C—$R_1$
  B represents nitrogen or C—$R_2$;
  C represents nitrogen or C—$R_3$;
  D represents nitrogen or C—$R_4$ with the proviso that at least one but not more than 2 of the group A, B, C, D are nitrogen; and
  E represents oxygen, sulfur or N—$R_5$;
  $R_1$ through $R_4$ are the same or different and represent
    hydrogen, halogen, cyano, trifluoromethyl, trifluoromethoxy, hydroxy, straight or branched chain lower alkyl having 1–6 carbon atoms, amino, mono or dialkylamino where each alkyl is straight or branched chain lower alkyl having 1–6 carbon atoms, or straight or branched chain lower alkoxy having 1–6 carbon atoms:
  $R_5$ is
    hydrogen or straight or branched chain lower alkyl having 1–6 carbon atoms, or phenyl, thienyl, or pyridyl, each of which may be mono or disubstituted with halogen, cyano, trifluoromethyl, trifluoromethoxy, hydroxy, straight or branched chain lower alkyl having 1–6 carbon atoms, amino, mono or dialkylamino where each alkyl is straight or branched chain lower alkyl having 1–6 carbon atoms, or straight or branched chain lower alkoxy having 1–6 carbon atoms;

X is

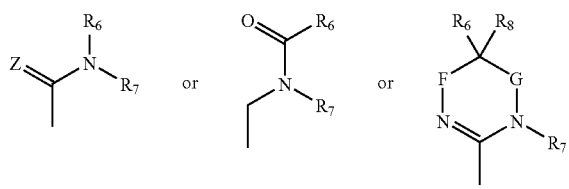

F is
carbonyl, methyene or ethylene
G is
methylene or a carbon—carbon single bond with the proviso that G is a carbon—carbon single bond when F is ethylene
Z is
oxygen, sulfur, N—C≡N, or two hydrogen atoms;

$R_6$ is
phenyl, thienyl, or pyridyl, each of which may be mono or disubstituted with halogen, cyano, trifluoromethyl, trifluoromethoxy, hydroxy, straight or branched chain, lower alkyl having 1–6 carbon atoms, amino, mono or dialkylamino where each alkyl is straight or branched chain lower alkyl having 1–6 carbon atoms, or straight or branched chain lower alkoxy having 1–6 carbon atoms; or $R_6$ is
straight or branched alkyl consisting of 1–8 carbons or cycloalkyl containing 3 to 8 carbon atoms wherein these groups may be mono or disubstituted with an aromatic ring such as phenyl or pyridyl and the aromatic groups can be mono or disubstituted with halogen, cyano, trifluoromethyl, trifluoromethoxy, hydroxy, straight or branched chain lower alkyl having 1–6 carbon atoms, amino, mono or disubstituted amino where the substituent on nitrogen is either a straight or branched chain having 1–6 carbon atoms, or straight or branched chain lower alkoxy having 1–6 carbon atoms; or $R_6$ is
is cycloalkyl containing 5 to 8 carbon atoms wherein the cycloalkyl is fused to an aromatic ring at adjacent positions;

$R_7$ and $R_8$ are the same or different and represent
hydrogen or straight or branched chain lower alkyl having 1–6 carbon atoms; or $R_6$ and $R_7$ taken together may form a 5, 6, 7 or 8 membered ring which is mono or disubstituted with an aryl group or contains a fused aryl ring as part of the 5,6, 7 or 8 membered ring described above with the proviso that $R_6$, and $R_7$ taken together do not form a ring when G is a methylene; or $R_1$ and $R_8$ taken together may form a 5, 6, 7 or 8 membered ring which is mono or disubstituted with an aryl group or contains a fused aryl ring as part of the 5.6, 7 or 8 membered ring.

Compounds of formula I may have one or more asymmetric centers and may therefore exist in more than one stereoisomeric form. All stereoisomeric forms and mixtures thereof are encompassed in this application.

This invention also includes methods for using compounds of formula I to treat diseases and disorders in mammals in which activation of NK-3 receptors is of importance.

These compounds are highly selective agonists or, preferably, antagonists at NK3 receptors.

DETAILED DESCRIPTION OF THE INVENTION

The novel compounds encompassed by the instant invention are described by general formula I as set forth above. Specific compounds of the invention include those of Formula IIa:

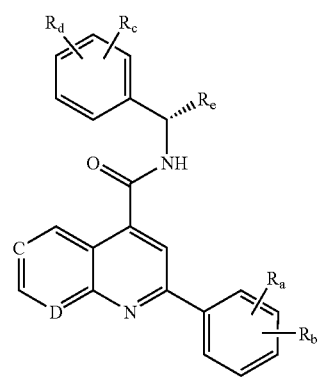

IIa where

C and D are independently CH or N, provided that not both C and D are N simultaneously;

$R_a$ and $R_b$ are independently hydrogen, halogen, cyano, trifluoromethyl, trifluoromethoxy, hydroxy, $C_1$–$C_6$ alkyl, $C_1$–$C_6$ alkoxy, amino, or mono or dialkylamino where each alkyl independently $C_1$–$C_6$ alkyl;

$R_c$ and $R_d$ are independently hydrogen, halogen, cyano, trifluoromethyl, trifluoromethoxy, hydroxy, $C_1$–$C_6$ alkyl, $C_1$–$C_6$ alkoxy, amino, or mono or dialkylamino where each alkyl independently $C_1$–$C_6$ alkyl; and $R_e$ is $C_1$–$C_6$ alkyl, preferably $C_1$–$C_4$ alkyl, more preferably methyl, ethyl or propyl.

Preferred compounds of Formula IIa are those where D is CH, C is nitrogen, and $R_a$, $R_b$, $R_c$, and $R_d$ are hydrogen. Other preferred compounds of of Formula IIa are those where C is CH, D is nitrogen, $R_a$ and $R_b$, are hydrogen and $R_c$ is ethyl. Other preferred compounds of Formula IIa are those where both C and D are CH. $R_a$ and $R_b$ are hydrogen and $R_c$ is ethyl.

Further specific compounds of the invention include those of Formula IIb:

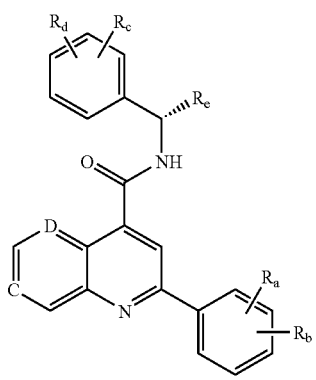

where

C and D are independently CH or N, provided that not both C and D are N simultaneously;

$R_a$ and $R_b$ are independently hydrogen, halogen, cyano, trifluoromethyl, trifluoromethoxy, hydroxy, $C_1$–$C_6$ alkyl, $C_1$–$C_6$ alkoxy, amino, or mono or dialkylamino where each alkyl independently $C_1$–$C_6$ alkyl;

$R_c$ and $R_d$ are independently hydrogen, halogen, cyano, trifluoromethyl, trifluoromethoxy, hydroxy, $C_1$–$C_6$ alkyl, $C_1$–$C_6$ alkoxy, amino, or mono or dialkylamino where each alkyl independently $C_1$–$C_6$ alkyl; and $R_c$ is $C_1$–$C_6$ alkyl, preferably $C_1$–$C_4$ alkyl, more preferably methyl, ethyl or propyl.

Preferred compounds of Formula IIb are those where D is CH, C is nitrogen, and $R_a$, $R_b$, $R_c$, and $R_d$ are hydrogen. Other preferred compounds of of Formula IIb are those where C is CH, D is nitrogen, $R_a$ and $R_b$ are hydrogen and $R_c$ is ethyl. Other preferred compounds of Formula IIb are those where both C and D are CH, $R_a$ and $R_b$ are hydrogen and $R_c$ is ethyl.

Other specific compounds of the invention include those of Formula III:

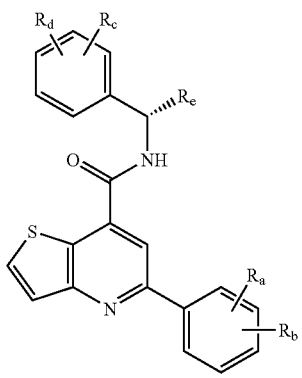

where $R_a$ and $R_b$ are independently hydrogen, halogen, cyano, trifluoromethyl, trifluoromethoxy, hydroxy, $C_1$–$C_6$ alkyl, $C_1$–$C_6$ alkoxy, amino, or mono or dialkylamino where each alkyl independently $C_1$–$C_6$ alkyl;

$R_c$ and $R_d$ are independently hydrogen, halogen, cyano, trifluoromethyl, trifluoromethoxy, hydroxy, $C_1$–$C_6$ alkyl, $C_1$–$C_6$ alkoxy, amino, or mono or dialkylamino where each alkyl independently $C_1$–$C_6$ alkyl; and $R_c$ is $C_1$–$C_6$ alkyl, preferably $C_1$–$C_4$ alkyl, more preferably methyl, ethyl or propyl.

Preferred compounds of Formula III are those where $R_a$ and $R_b$ are hydrogen and $R_c$ is ethyl.

Other specific compounds of the invention include those of Formula IVa:

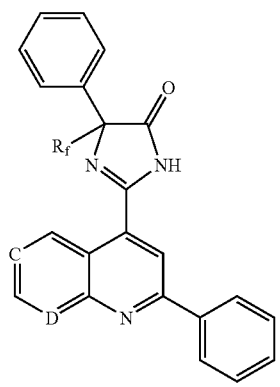

where

C and D are independently CH or N, provided that not both C and D are N simultaneously;

$R_f$ is hydrogen or $C_1$–$C_6$ alkyl, preferably methyl or ethyl;

$R_a$ and $R_b$ are independently hydrogen, halogen, cyano, trifluoromethyl, trifluoromethoxy, hydroxy, $C_1$–$C_6$ alkyl, $C_1$–$C_6$ alkoxy, amino, or mono or dialkylamino where each alkyl independently $C_1$–$C_6$ alkyl; and $R_c$ and $R_d$ are independently hydrogen, halogen, cyano, trifluoromethyl, trifluoromethoxy, hydroxy, $C_1$–$C_6$ alkyl, $C_1$–$C_6$ alkoxy, amino, or mono or dialkylamino where each alkyl independently $C_1$–$C_6$ alkyl.

Preferred compounds of Formula IVa are those where $R_a$ and $R_b$, are hydrogen and $R_f$ is ethyl.

Still other specific compounds of the invention include those of Formula IVb:

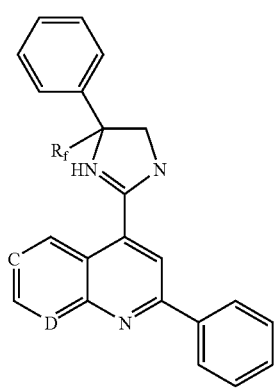

where

C and D are independently CH or N, provided that not both C and D are N simultaneously;

$R_f$ is hydrogen or $C_1$–$C_6$ alkyl, preferably methyl or ethyl;

$R_a$ and $R_b$ are independently hydrogen, halogen, cyano, trifluoromethyl, trifluoromethoxy, hydroxy, $C_1$–$C_6$ alkyl, $C_1$–$C_6$ alkoxy, amino, or mono or dialkylamino where each alkyl independently $C_1$–$C_6$ alkyl; and $R_c$ and $R_d$ are independently hydrogen, halogen, cyano, trifluoromethyl, trifluoromethoxy, hydroxy, $C_1$–$C_6$ alkyl, $C_1$–$C_6$ alkoxy, amino, or mono or dialkylamino where each alkyl independently $C_1$–$C_6$ alkyl.

Preferred compounds of Formula IVb are those where $R_a$ and $R_b$ are hydrogen and $R_f$ is ethyl.

Compounds of formula I may have one or more asymmetric centers and may therefore exist in more than one stereoisomeric form. All stereoisomeric forms and mixtures thereof are encompassed in this application.

This invention also includes methods for using compounds of formula I to treat diseases and disorders in mammals in which activation of NK-3 receptors is of importance.

Non-toxic pharmaceutical salts include salts of acids such as hydrochloric, phosphoric, hydrobromic, sulfuric, sulfinic, formic, toluene sulfonic, hydroiodic, acetic and the like. Those skilled in the art will recognize a wide variety of non-toxic pharmaceutically acceptable addition salts.

Representative compounds of the present invention are those of Formula I and their pharmaceutically acceptable salts. The present invention also encompasses the acylated prodrugs of the compounds of Formula I. Those skilled in the art will recognize various synthetic methodologies that may be employed to prepare non-toxic pharmaceutically acceptable addition salts and acylated prodrugs of the compounds encompassed by Formula I.

By "lower alkyl" and "alkyl" in the present invention is meant straight or branched chain alkyl groups having 1–6 carbon atoms, such as, for example, methyl, ethyl, propyl, isopropyl, n-butyl, sec-butyl, tert-butyl, pentyl, 2-pentyl, isopentyl, neopentyl, hexyl, 2-hexyl, 3-hexyl, and 3-methylpentyl.

By "lower alkoxy" and "alkoxy" in the present invention is meant straight or branched chain alkoxy groups having 1–6 carbon atoms, such as, for example, methoxy, ethoxy, propoxy, isopropoxy, n-butoxy, sec-butoxy, tert-butoxy, pentoxy, 2-pentyl, isopentoxy, neopentoxy, hexoxy, 2-hexoxy, 3-hexoxy, and 3-methylpentoxy.

By halogen in the present invention is meant fluorine, bromine, chlorine, and iodine.

Where a substituent, such as, for example, W, represents groups such as piperidinyl, morpholinyl, thiomorpholinyl, pyrrolindinyl, piperazinyl, homopiperazinyl, azabicyclo[3.2.2]nonanyl, and isoindolinyl, those groups are preferably covalently coupled to the parent structure by a nitrogen atom in the group. Further, the specific groups recited in this paragraph may unsubstituted, or mono or disubstituted with alkyl or aryl groups, or fused to an aromatic ring. Where they are fused to an aromatic ring, the aromatic ring is preferably a benzo, pyridino, pyrimidino, pyridazino, or pyrazino group.

By "aromatic" as used herein is meant both aryl and heteroaryl groups.

By "hetroaryl" (aromatic heterocycle) as used herein is meant one or more aromatic ring systems of 5-, 6-, or 7-membered rings containing at least one and up to four hetero atoms selected from nitrogen, oxygen, or sulfur. Such heteroaryl groups include, for example, thienyl, furanyl, thiazolyl, imidazolyl, (is)oxazolyl, pyridyl, pyrimidinyl, (iso)quinolinyl, naphthyridinyl, benzimidazolyl, and benzoxazolyl.

By "heterocycle having aromatic character" as used herein is meant the heteroaryl groups described above and also bicyclic ring systems where at least one of the rings is aromatic. Examples of such bicyclic ring systems include pyridazinomorpholinyl, pyridinomorpholinyl, 2–2,3,4-trihydropyranopyridinyl, 5,67,8-tetrahydropyridinopyrimidinyl, 5,6,7,8-tetrahydroquinazolinyl, 5,6,7,8-tetrahydroisoquinolyl, 5,6,7,8,9-pentahydrocycloheptapyridinyl, and 1H,2H,3H,4H,5H-pyridinoazepinyl.

By aryl is meant an aromatic carbocyclic group having a single ring (e.g., phenyl), multiple rings (e.g., biphenyl), or multiple condensed rings in which at least one is aromatic, (e.g., 1,2,3,4-tetrahydronaphthyl, naphthyl, anthryl, or phenanthryl), which is optionally mono-, di-, or trisubstituted with, e.g., halogen, lower alkyl, lower alkoxy, trifluoromethyl, hydroxy, mono- or di-alkylamino. Preferred aryl groups are optionally substituted phenyl groups.

Representative compounds of the invention are shown below in Table 1.

TABLE 1

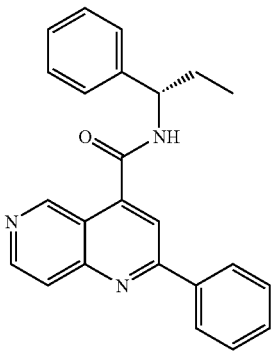

Compound 1

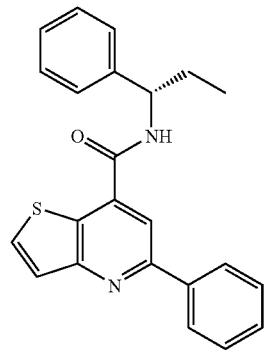

Compound 2

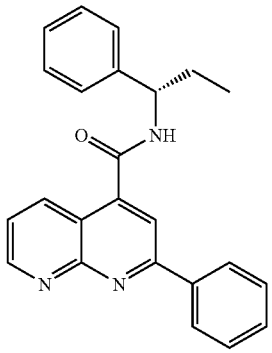

Compound 3

The compounds of general Formula I may be administered orally, topically, parenterally, by inhalation or spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition, there is provided a pharmaceutical formulation comprising a compound of general Formula I and a pharmaceutically acceptable carrier. One or more compounds of general Formula I may be present in association with one or more non-toxic pharmaceutically acceptable carriers and/or diluents and/or adjuvants and if desired other active ingredients. The pharmaceutical compositions containing compounds of general Formula I may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydropropylmethylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monoleate, and condensation products of the said partial esters with ethylene oxide, for example polyoxyethylene sorbitan monoleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using suitable dispersing or wetting agents and suspending agents, such as those mentioned above. The sterile injectable preparation may also be a solution or suspension in a non-toxic parentally acceptable diluent or solvent, for example as a solution in 1,3-butanediol. Among the acceptable vehicles and solvents that may be employed are water, isotonic aqueous sodium chloride solutions, Ringer's solution and other buffered isotonic salt solutions. In addition, sterile, fixed oils are conventionally employed as a solvent or suspending medium. For this purpose any bland fixed oil may be employed including synthetic mono-or diglycerides. In addition, fatty acids such as oleic acid find use in the preparation of injectables.

The compounds of general Formula I may also be administered in the form of suppositories for rectal administration of the drug. These compositions can be prepared by mixing the drug with a suitable non-irritating excipient, which is solid at ordinary temperatures but liquid at the body temperature and will therefore melt internally to release the drug. Such materials include cocoa butter and polyethylene glycols.

Compounds of general Formula I may be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

Dosage levels of the order of from about 0.1 mg to about 140 mg, preferably between about 1 mg to about 70 mg, per kilogram of body weight per day are typically useful in the treatment of the above-indicated conditions (preferably between about 5 mg to about 5 g per patient per day). The amount of active ingredient that may be combined with the carrier materials to produce a single dosage form will vary depending upon the host treated and the particular mode of administration. Dosage unit forms will generally contain between from about 1 mg to about 1 g of an active ingredient.

Frequency of dosage may also vary depending on the compound used and the particular disease treated. However, for treatment of most CNS disorders, a dosage regimen of 4 times daily or less is preferred. For the treatment of schizoprenia and depression a dosage regimen of 1 or 2 times daily is particularly preferred.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

Preferred compounds of the invention will have certain pharmacological properties. Such properties include, but are not limited to oral bioavailability, low toxicity, low serum protein binding and desirable in vitro and in vivo half-lifes. Penetration of the blood brain barrier for compounds used to treat CNS disorders is necessary, while low brain levels of compounds used to treat periphereal disorders are often preferred.

Assays may be used to predict these desirable pharmacological properties. Assays used to predict bioavailability include transport across human intestinal cell monolayers, including Caco-2 cell monolayers. Toxicity to cultured hepatocyctes may be used to predict compound toxicity. Penetration of the blood brain barrier of a compound in humans may be predicted from the brain levels of the compound in laboratory animals given the compound intravenously.

Serum protein binding may be predicting from albumin binding assays. Such assays are described in a review by Oravcová, et al. (Journal of Chromatography B (1996) volume 677, pages 1–27).

Compound half-life is inversely proportional to the frequency of dosage of a compound. In vitro half-lifes of compounds may be predicted from assays of microsomal half-life as described by Kuhnz and Gieschen (Drug Metabolism and Disposition, (1998) volume 26, pages 1120–1127).

The present invention also pertains to packaged pharmaceutical compositions for treating disorders responsive to NK-3 receptor modulation, e.g., schizoprenia or depression.

The packaged pharmaceutical compositions include a container holding a therapeutically effective amount of at least one NK-3 receptor ligand as described supra and instructions (e.g., labeling) indicating that the contained NK-3 receptor ligand is to be used for treating a disorder responsive to NK-3 receptor modulation in a patient.

The present invention also pertains to methods of inhibiting the binding of a neurokinin to the NK-3 receptor which methods involve contacting a compound of the invention with cells expressing NK-3 receptors, wherein the compound is present at a concentration sufficient to inhibit neurokinin binding to cells expressing a cloned human NK3 receptor in vitro and to methods for altering the signaltransducing activity of NK-3 receptors, said method comprising exposing cells expressing such receptors to an effective amount of a compound of the invention.

An illustration of the preparation of compounds of the present invention is given in Schemes 1, 2, and 3. The various substituents in Schemes 1, 2, and 3 are defined as above for Formula I.

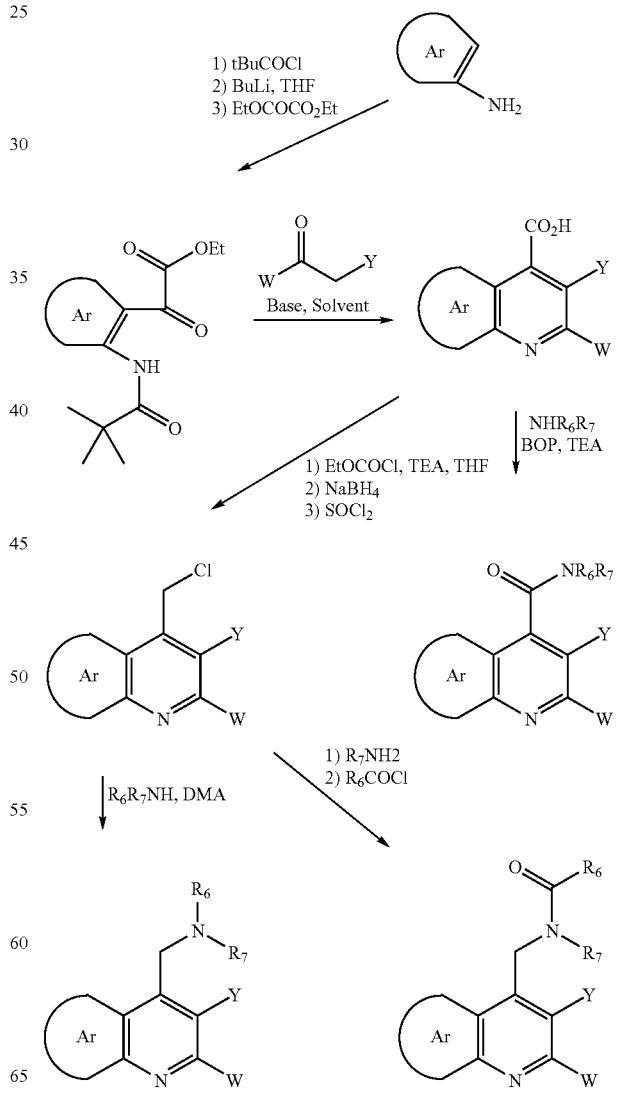

Scheme 1

15

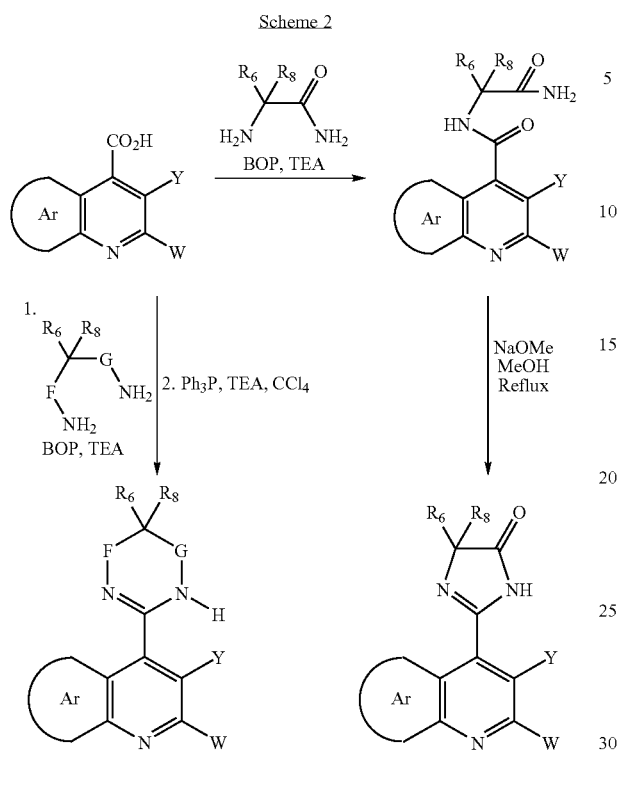

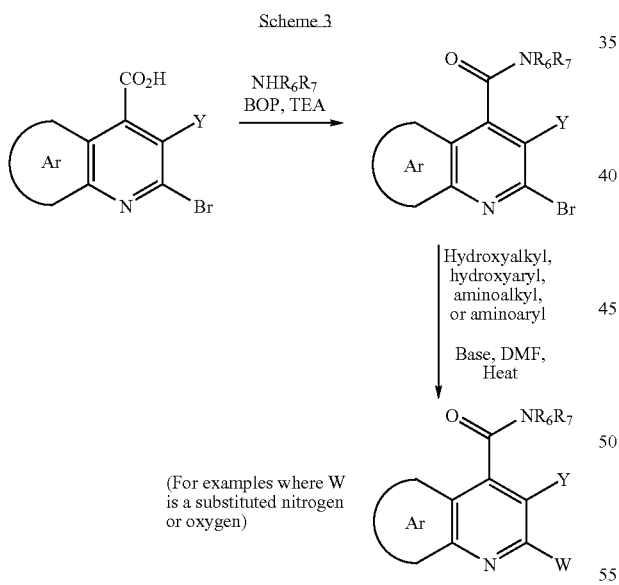

Those having skill in the art will recognize that the starting materials may be varied and additional steps employed to produce compounds encompassed by the present invention, as demonstrated by the following examples. In some cases protection of certain reactive functionalities may be necessary to achieve some of the above transformations. In general the need for such protecting groups will be obvious to those skilled in the art of organic synthesis as well as the conditions necessary to attach and remove such groups.

16

The invention is illustrated further by the following examples, which are not to be construed as limiting the invention in scope or spirit to the specific procedures described in them.

EXAMPLE I

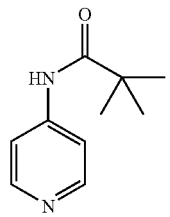

To a mixture of 20 g of 4-Aminopyridine and 37 mL of triethylamine in 380 mL of methylene chloride is added 28.8 mL of pivaloyl chloride in a dropwise fashion. After 1 hour at room temperature the reaction mixture is washed with water and sodium bicarbonate solution, dried over magnesium sulfate and the solvent is removed in vacuo. The residue is triturated with hexane to afford 4-trimethylacetamidopyridine as a white solid.

EXAMPLE II

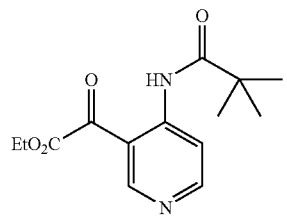

A solution of 10 g of 4-trimethylacetamido pyridine in 150 mL of dry tetrahydrofuran is cooled to −78° C. and 88 mL of 1.6M n-butyllithium in hexane is added in a dropwise fashion. The mixture is then stirred at 0° C. for 3 hours, cooled again to −78° C. and 21.3 g of diethyl oxalate dissolved in 190 mL of tetrahydrofuran is added in a dropwise fashion, the reaction mixture was then gradually allowed to come to room temperature. The reaction mixture is diluted with water and the product is extracted with ether. After drying over magnesium sulfate the solvent is removed in vacuo. The residue is chromatagraphed on silica gel with hexane/ether 2:1 as the eluent to afford ethyl 4-trimethylacetamido-3-pyridylpyruvate as an orange oil.

EXAMPLE III

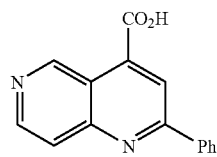

A mixture of 3.59 g of ethyl 4-trimethylacetamido-3-pyridylpyruvate, 2.89 g of potassium hydroxide in 10 mL of ethanol and 40 mL of water is heated at reflux for 2 hours. At this time 3.1 g of acetophenone is added and refluxing is continued for 6 hours. The ethanol is removed in vacuo, the resulting aqueous solution is washed with ether and the aqueous layer is acidified to pH5. The product is collected washed with water and dried to afford (2-phenylpyridino[4,3-b]pyridin-4-yl) carboxylic acid as a white solid.

EXAMPLE IV

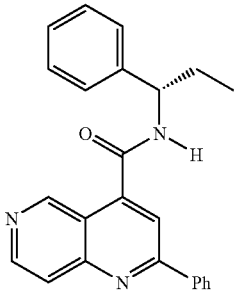

Compound 1

To a solution of 250 mg of 2-phenylpyridino[4,3-b]pyridin-4-yl carboxylic acid dissolved in 5 mL of dimethylacetamide and 200 uL of triethylamine is added 500 mg of BOP in 5 mL of dichloroethane followed by 150 mg of (S)-1-phenylpropylamine. The reaction mixture is stirred for 16 hours at room temperature. The reaction mixture is poured onto 50 mL of 1N NaOH and the product is extracted with 25 mL of ethyl acetate. After drying over magnesium sulfate the solvent is removed in vacuo to afford N—[(S)-1-phenyl-1-propyl)]-(2-phenylpyridino[4,3-b]pyridin-4-yl) carboxamide as a solid.

EXAMPLE V

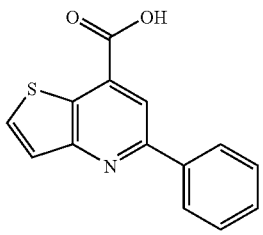

Prepare 2-phenylthieno[3,2-b]pyridin-4-yl chloride by the method described in PCT application WO 9943682. A mixture containing 400 mg of 2-phenylthieno[3,2-b]pyridin-4-yl chloride, 400 mg of p-toluenesulfonic acid and 200 mg of potassium cyanide in anhydrous DMF is heated at 160° C. in an oil bath for 16 h under nitrogen. The mixture is cooled to ambient temperature, poured into a mixture of ice and water. The resulting mixture is extracted with ethyl acetate and the ethyl acetate layer is washed with water followed by brine. The ethyl acetate solution is dried over sodium sulfate, filtered and evaporated at reduced pressure to obtain a tan-colored residue. This material is dissolved in 10 ml of ethanol, treated with 1 g of sodium hydroxide and heated at reflux for 2 h. The ethanol solution is evaporated and the resulting residue is dissolved in water. The pH of this solution is adjusted to slightly acidic by addition of 1 N HCl to yield 2-phenylthieno[3,2-b]pyridin-4-yl carboxylic acid as a red-orange solid. After drying in vacu this material is pure according to proton NMR and LC/MS.

EXAMPLE VI

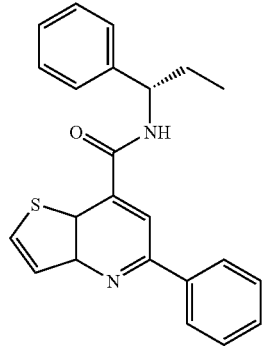

Compound 2

A mixture containing 100 mg of 2-phenylthieno[3,2-b]pyridin-4-yl carboxylic acid, 66 mg of (S)-1-phenylpropylamine, 43 µl of N-methylmorpholine and 79 mg of hydroxybenzotriazole (HOBT) in 8 ml of 7:3 tetrahydrofuran/acetonitrile is cooled to −5° C. Add 580 µl of 1 mM solution of dicyclohexylcarbodiimide (DCC) in tetrahydrofuan. Stir at room temperature for 17 h. Filter to remove solids and evaporate the filtrate at reduced pressure to obtain an orange solid. Purify by chromatography on silica gel eluting with 20% ethyl acetate in hexane to obtain a cream-colored solid. TLC (20% ethyl acetate/hexane) Rf=0.29. LC/MS m/z M+1=373.

EXAMPLE VII

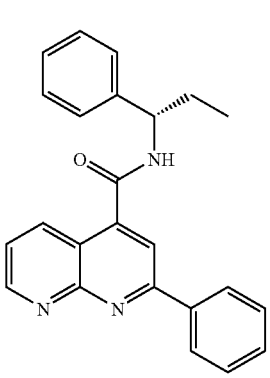

Compound 3

The required 2-phenylpyridino[2,3-b]pyridin-4-yl carboxylic acid is prepared from 3-aminopyridine according to the procedures outlined in Examples I–III. A mixture containing 100 mg of 2-phenylpyridino[2,3-b]pyridin-4-yl carboxylic acid, 68 mg of (S)-1-phenylpropylamine, 44 µl of N-methylmorpholine and 81 mg of hydroxybenzotriazole (HOBT) in 8 ml of 7:3 tetrahydrofuran/acetonitrile is cooled to −5° C. Add 600 µl of 1 mM solution of dicyclohexylcarbodiimide (DCC) in tetrahydrofuan. Stir at room temperature for 17 h. Filter to remove solids and evaporate the filtrate at reduced pressure. Dilute with 10 ml of dichloromethane, let stand 1 hour and again remove solids by filtration. Evaporate the filtrate and purify by chromatography on silica gel eluting with 3% methanol in dichloromethane with 0.5% ammonium hydroxide as additive to obtain a white solid. TLC (5% methanol/dichloromethane/ 0.5% ammonium hydroxide) Rf=0.45. LC/MS m/z M+1=368.

EXAMPLE VIII

Additional compounds of the invention, prepared as described in Schemes 1–3 are shown in Table 2a, Table 2b and Table 2c.

The compounds in TABLES 2a and 2b are prepared according to Scheme I using the following conditions: A quantity of 0.1 mL of a 0.2 M acid solution in DMA:TEA is added to 0.1 mL of a 0.2M amine solution in Toluene:NMM, and 0.15 mL of a 0.2 M BOP reagent solution in dichloroethane. The mixture is heated for 3 hrs at 50° C. At which time the solution is cooled to room temperature. The mixture is partitioned between 1N NaOH and ethyl acetate. The ethyl acetate layer is chromatographed on silica gel with ethyl acetate to afford the desired compound.

Analysis is performed on a Hewlett Packard 6890 GC, equipped with a dual cool on-column inlets and flame ionization detectors or mass spectrometer detectors. All gas flows are regulated via electronic pneumatic control. The analytical column used is a Supelco PTE-5 QTM, 15 m×0.53 mm ID×0.50 μm film. GC instrument control and data collection are handled using a Perkin Elmer Turbo-Chrom Client/Server data system. GC conditions: On-column injector 163° C. for 2.5 min., ramp at 40° C./min to 323° C. Oven program 100° C. for 1 minute, ramp at 40° C./min to 320° C. Detector temperature is set at 325° C.

In Table 2a, $X_1$ is a group of the Formula:

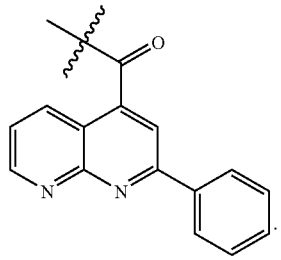

In Table 2b, $X_1$ represents a group of the formula:

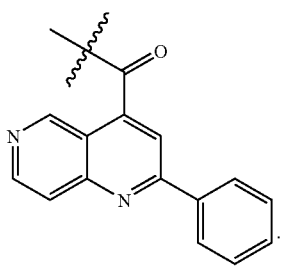

TABLE 2a

| Compound | Name | GC Retention Time (min) |
|---|---|---|
| H₃C—CH(Ph)—N(CH₃)—X₁ | N-[1-(phenyl)ethyl]-N-methyl(2-phenylpyridino[2,3-b]pyridin-4-yl)carboxamide | 6.4 |
| X₁—N(CH₃)—CH(Ph)—CH₂—CH₂—CH₃ | N-[1-(phenyl)butyl]-N-methyl(2-phenylpyridino[2,3-b]pyridin-4-yl)carboxamide | 6.53 |
| X₁—N(CH₃)—CH(Ph)—CH₂—CH₂—CH₂—CH₃ | N-[1-(phenyl)pentyl]-N-methyl(2-phenylpyridino[2,3-b]pyridin-4-yl)carboxamide | 6.65 |

TABLE 2a-continued

| Compound | Name | GC Retention Time (min) |
|---|---|---|
| 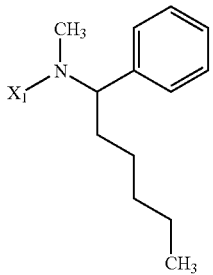 | N-[1-(phenyl)hexyl]-N-methyl(2-phenylpyridino[2,3-b]pyridin-4-yl)carboxamide | 6.77 |
| 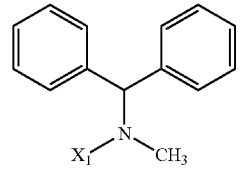 | N-[1-(diphenyl)methyl]-N-methyl(2-phenylpyridino[2,3-b]pyridin-4-yl)carboxamide | 7.17 |
| 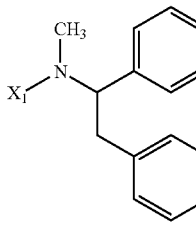 | N-[1-(1,2-diphenyl)ethyl]-N-methyl(2-phenylpyridino[2,3-b]pyridin-4-yl)carboxamide | 7.57 |
| 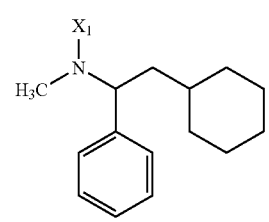 | N-[1-(1-phenyl-2-cyclohexyl)ethyl]-N-methyl(2-phenylpyridino[2,3-b]pyridin-4-yl)carboxamide | 7.36 |
| 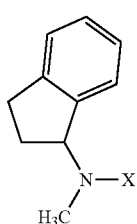 | N-indanyl-N-methyl(2-phenylpyridino[2,3-b]pyridin-4-yl)carboxamide | 6.76 |
| 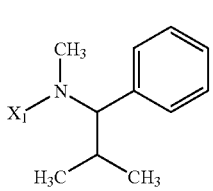 | N-[1-(phenyl)isobutyl]-N-methyl(2-phenylpyridino[2,3-b]pyridin-4-yl)carboxamide | 6.47 |

TABLE 2a-continued

| Compound | Name | GC Retention Time (min) |
|---|---|---|
| 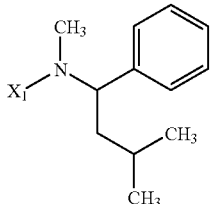 | N-[1-(phenyl)2-methylbutyl]-N-methyl(2-phenylpyridino[2,3-b]pyridin-4-yl)carboxamide | 6.52 |
| 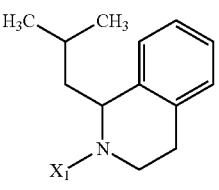 | 1-isobutyl(2-1,2,3,4-tetrahydroisoquinolyl)(2-phenylpyridino[2,3-b]pyridin-4-yl)ketone | 6.83 |
| 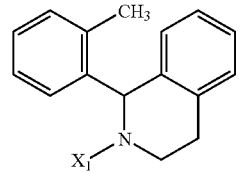 | 1-(2-methylphenyl)(2-1,2,3,4-tetrahydroisoquinolyl)(2-phenylpyridino[2,3-b]pyridin-4-yl)ketone | 8.03 |
| 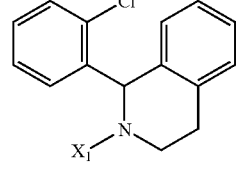 | 1-(2-chlorophenyl)(2-1,2,3,4-tetrahydroisoquinolyl)(2-phenylpyridino[2,3-b]pyridin-4-yl)ketone | 8.46 |
| 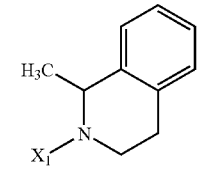 | 1-methyl(2-1,2,3,4-tetrahydroisoquinolyl)(2-phenylpyridino[2,3-b]pyridin-4-yl)ketone | 6.72 |
| 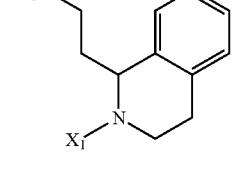 | 1-propyl(2-1,2,3,4-tetrahydroisoquinolyl)(2-phenylpyridino[2,3-b]pyridin-4-yl)ketone | 6.85 |
| 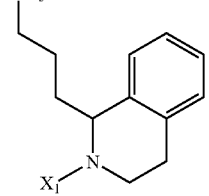 | 1-butyl(2-1,2,3,4-tetrahydroisoquinolyl)(2-phenylpyridino[2,3-b]pyridin-4-yl)ketone | 6.97 |

TABLE 2a-continued

| Compound | Name | GC Retention Time (min) |
|---|---|---|
| | 1-cyclopentyl(2-1,2,3,4-tetrahydroisoquinolyl)(2-phenylpyridino[2,3-b]pyridin-4-yl)ketone | 7.5 |
| | 1-pentyl(2-1,2,3,4-tetrahydroisoquinolyl)(2-phenylpyridino[2,3-b]pyridin-4-yl)ketone | 7.15 |
| | 1-benzyl(2-1,2,3,4-tetrahydroisoquinolyl)(2-phenylpyridino[2,3-b]pyridin-4-yl)ketone | 8.14 |
| | 1-cyclohexylmethyl(2-1,2,3,4-tetrahydroisoquinolyl)(2-phenylpyridino[2,3-b]pyridin-4-yl)ketone | 7.92 |
| | 1-isopropyl(2-1,2,3,4-tetrahydroisoquinolyl)(2-phenylpyridino[2,3-b]pyridin-4-yl)ketone | 6.81 |
| | N-[1-(phenyl)octyl]-N-methyl(2-phenylpyridino[2,3-b]pyridin-4-yl)carboxamide | 6.82 |

TABLE 2a-continued

| Compound | Name | GC Retention Time (min) |
|---|---|---|
| 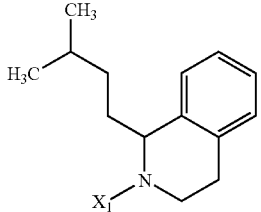 | 1-(2-methylbutyl)(2-1,2,3,4-tetrahydroisoquinolyl)(2-phenylpyridino[2,3-b]pyridin-4-yl)ketone | 6.76 |
| 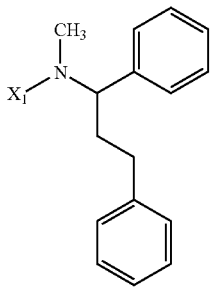 | N-[1,3-(diphenyl)propyl]-N-methyl(2-phenylpyridino[2,3-b]pyridin-4-yl)carboxamide | 7.37 |
| 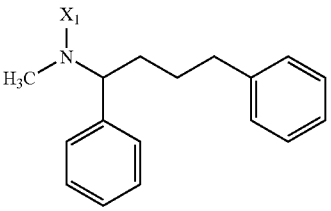 | N-[1,4-(diphenyl)butyl]-N-methyl(2-phenylpyridino[2,3-b]pyridin-4-yl)carboxamide | 7.66 |
| 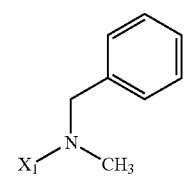 | N-benzyl-N-methyl(2-phenylpyridino[2,3-b]pyridin-4-yl)carboxamide | 6.13 |
| 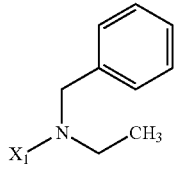 | N-benzyl-N-ethyl(2-phenylpyridino[2,3-b]pyridin-4-yl)carboxamide | 6.15 |
| 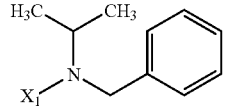 | N-benzyl-N-isopropyl(2-phenylpyridino[2,3-b]pyridin-4-yl)carboxamide | 6.15 |
| 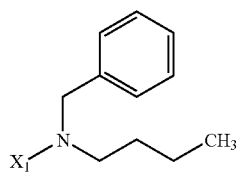 | N-benzyl-N-butyl(2-phenylpyridino[2,3-b]pyridin-4-yl)carboxamide | 6.3 |

TABLE 2a-continued

| Compound | Name | GC Retention Time (min) |
|---|---|---|
| | N-benzyl-N-isobutyl(2-phenylpyridino[2,3-b]pyridin-4-yl)carboxamide | 6.2 |
| | N-benzyl-N-cyclopentyl(2-phenylpyridino[2,3-b]pyridin-4-yl)carboxamide | 6.59 |
| | N-benzyl-N-pentyl(2-phenylpyridino[2,3-b]pyridin-4-yl)carboxamide | 6.41 |
| | N-benzyl-N-cyclohexyl(2-phenylpyridino[2,3-b]pyridin-4-yl)carboxamide | 6.35 |
| | N,N-dibenzyl(2-phenylpyridino[2,3-b]pyridin-4-yl)carboxamide | 6.43 |
| | N-benzyl-N-1-methylpropyl(2-phenylpyridino[2,3-b]pyridin-4-yl)carboxamide | 6.44 |
| | N-benzyl-N-1-methylbutyl(2-phenylpyridino[2,3-b]pyridin-4-yl)carboxamide | 6.84 |

TABLE 2a-continued

| Compound | Name | GC Retention Time (min) |
|---|---|---|
| | N-benzyl-N-4-methylbutyl(2-phenylpyridino[2,3-b]pyridin-4-yl)carboxamide | 6.66 |
| | N-benzyl-N-cyclopentylmethyl(2-phenylpyridino[2,3-b]pyridin-4-yl)carboxamide | 7.03 |
| | N-benzyl-N-hexyll(2-phenylpyridino[2,3-b]pyridin-4-yl)carboxamide | 6.82 |
| | N-benzyl-N-cyclohexylmethyl(2-phenylpyridino[2,3-b]pyridin-4-yl)carboxamide | 7.33 |
| | N-benzyl-N-heptyl(2-phenylpyridino[2,3-b]pyridin-4-yl)carboxamide | 7.59 |
| | N-methyl(2-phenylpyridino[2,3-b]pyridin-4-yl)carboxamide | 5.51 |
| | N-[1-(phenylcyclopentyl)methyl]-N-methyl(2-phenylpyridino[2,3-b]pyridin-4-yl)carboxamide | 6.92 |
| | N-[1-(phenylcyclohexyl)methyl]-N-methyl(2-phenylpyridino[2,3-b]pyridin-4-yl)carboxamide | 7.11 |

TABLE 2a-continued

| Compound | Name | GC Retention Time (min) |
|---|---|---|
| | N-[1-(1-phenyl-2cyclopentyl)ethyl]-N-methyl(2-phenylpyridino[2,3-b]pyridin-4-yl)carboxamide | 7.02 |
| | N-[1-(1,3-diphenyl)propyl]-N-methyl(2-phenylpyridino[2,3-b]pyridin-4-yl)carboxamide | 7.63 |
| | N-[1-(1,4-diphenyl)butyl]-N-methyl(2-phenylpyridino[2,3-b]pyridin-4-yl)carboxamide | 7.99 |
| | 1-phenyl(2-1,2,3,4-tetrahydroisoquinolyl)(2-phenylpyridino[2,3-b]pyridin-4-yl)ketone | 7.22 |
| | 1-cyclohexyl(2-1,2,3,4-tetrahydroisoquinolyl)(2-phenylpyridino[2,3-b]pyridin-4-yl)ketone | 7.23 |
| | 1-cyclopentylmethyl(2-1,2,3,4-tetrahydroisoquinolyl)(2-phenylpyridino[2,3-b]pyridin-4-yl)ketone | 7.09 |

TABLE 2a-continued

| Compound | Name | GC Retention Time (min) |
|---|---|---|
| (hexyl-tetrahydroisoquinoline structure) | 1-hexyl(2-1,2,3,4-tetrahydroisoquinolyl)(2-phenylpyridino[2,3-b]pyridin-4-yl)ketone | 6.9 |
| (2-fluorophenyl-tetrahydroisoquinoline structure) | 1-(2-fluorophenyl)(2-1,2,3,4-tetrahydroisoquinolyl)(2-phenylpyridino[2,3-b]pyridin-4-yl)ketone | 7.2 |
| (2-trifluoromethylphenyl-tetrahydroisoquinoline structure) | 1-(2-trifluoromethylphenyl)(2-1,2,3,4-tetrahydroisoquinolyl)(2-phenylpyridino[2,3-b]-pyridin-4-yl)ketone | 7.11 |
| (3-methylphenyl-tetrahydroisoquinoline structure) | 1-(3-methylphenyl)(2-1,2,3,4-tetrahydroisoquinolyl)(2-phenylpyridino[2,3-b]pyridin-4-yl)ketone | 7.77 |
| (4-methylphenyl-tetrahydroisoquinoline structure) | 1-(4-methylphenyl)(2-1,2,3,4-tetrahydroisoquinolyl)(2-phenylpyridino[2,3-b]pyridin-4-yl)ketone | 7.93 |
| (4-fluorophenyl-tetrahydroisoquinoline structure) | 1-(4-fluorophenyl)(2-1,2,3,4-tetrahydroisoquinolyl)(2-phenylpyridino[2,3-b]pyridin-4-yl)ketone | 7.58 |
| (cycloheptyl-tetrahydroisoquinoline structure) | 1-cycloheptyl(2-1,2,3,4-tetrahydroisoquinolyl)(2-phenylpyridino[2,3-b]pyridin-4-yl)ketone | 8.11 |

TABLE 2a-continued

| Compound | Name | GC Retention Time (min) |
|---|---|---|
|  | 1-(3-chlorophenyl)(2-1,2,3,4-tetrahydroisoquinolyl)(2-phenylpyridino[2,3-b]pyridin-4-yl)ketone | 8.27 |
|  | 1-(4-chlorophenyl)(2-1,2,3,4-tetrahydroisoquinolyl)(2-phenylpyridino[2,3-b]pyridin-4-yl)ketone | 8.39 |
|  | 6,7-dimethoxy(2-1,2,3,4-tetrahydroisoquinolyl)(2-phenylpyridino[2,3-b]pyridin-4-yl)ketone | 7.68 |
|  | 6,7-dimethoxy-1-methyl(2-1,2,3,4-tetrahydroisoquinolyl)(2-phenylpyridino[2,3-b]-pyridin-4-yl)ketone | 7.53 |
|  | 6,7-dimethoxy-1-phenyl(2-1,2,3,4-tetrahydroisoquinolyl)(2-phenylpyridino[2,3-b]-pyridin-4-yl)ketone | 9.16 |
|  | 6,7-dimethoxy-3-methyl(2-1,2,3,4-tetrahydroisoquinolyl)(2-phenylpyridino[2,3-b]-pyridin-4-yl)ketone | 7.51 |
|  | 2-[6,7-dimethoxy-2-(2-1,2,3,4-tetrahydroisoquinolyl)(2-phenylpyridino[2,3-b]pyridin-4-yl)]ethanenitrile ketone | 8.57 |
|  | N-[1-(4-bromophenyl)ethyl](2-phenylpyridino[2,3-b]pyridin-4-yl)carboxamide | 7.35 |

TABLE 2a-continued

| Compound | Name | GC Retention Time (min) |
|---|---|---|
| X₁-N-CH₂CH₂-C₆H₄-CH₃ (4-methyl) | N-[1-(4-methylphenyl)ethyl](2-phenylpyridino[2,3-b]pyridin-4-yl)carboxamide | 6.75 |
| X₁-N-CH₂CH₂-C₆H₄-CH₃ (3-methyl) | N-[1-(3-methylphenyl)ethyl](2-phenylpyridino[2,3-b]pyridin-4-yl)carboxamide | 6.71 |
| X₁-N-CH₂CH₂-C₆H₄-F (4-fluoro) | N-[1-(4-fluorophenyl)ethyl](2-phenylpyridino[2,3-b]pyridin-4-yl)carboxamide | 6.63 |
| X₁-N-CH₂CH₂-C₆H₄-F (3-fluoro) | N-[1-(3-fluorophenyl)ethyl](2-phenylpyridino[2,3-b]pyridin-4-yl)carboxamide | 6.63 |
| X₁-N-CH₂CH₂-C₆H₄-OCH₃ (4-methoxy) | N-[1-(4-methoxyphenyl)ethyl](2-phenylpyridino[2,3-b]pyridin-4-yl)carboxamide | 7.05 |
| 3-methoxyphenyl-CH₂CH₂-N-X₁ | N-[1-(3-methoxyphenyl)ethyl](2-phenylpyridino[2,3-b]pyridin-4-yl)carboxamide | 6.99 |
| X₁-N-CH₂CH₂-C₆H₄-Cl (4-chloro) | N-[1-(4-chlorophenyl)ethyl](2-phenylpyridino[2,3-b]pyridin-4-yl)carboxamide | 7.09 |
| X₁-N-CH₂CH₂-C₆H₄-Cl (3-chloro) | N-[1-(3-chlorophenyl)ethyl](2-phenylpyridino[2,3-b]pyridin-4-yl)carboxamide | 7.06 |
| X₁-N-CH₂CH₂-C₆H₄-CF₃ (4-trifluoromethyl) | N-[1-(4-trifluoromethylphenyl)ethyl](2-phenylpyridino[2,3-b]pyridin-4-yl)carboxamide | 6.6 |

TABLE 2a-continued

| Compound | Name | GC Retention Time (min) |
|---|---|---|
|  | N-[1-(3-trifluoromethylphenyl)ethyl](2-phenylpyridino[2,3-b]pyridin-4-yl)carboxamide | 6.54 |
|  | N-[1-(4-methylphenyl)methyl]-N-methyl(2-phenylpyridino[2,3-b]pyridin-4-yl)carboxamide | 6.17 |
|  | N-[1-(3-methylphenyl)methyl]-N-methyl(2-phenylpyridino[2,3-b]pyridin-4-yl)carboxamide | 6.13 |
|  | N-[1-(4-fluorophenyl)methyl]-N-methyl(2-phenylpyridino[2,3-b]pyridin-4-yl)carboxamide | 6.02 |
|  | N-[1-(3-fluorophenyl)methyl]-N-methyl(2-phenylpyridino[2,3-b]pyridin-4-yl)carboxamide | 6.01 |
|  | N-[1-(4-methoxyphenyl)methyl]-N-methyl(2-phenylpyridino[2,3-b]pyridin-4-yl)carboxamide | 6.41 |
|  | N-[1-(3-methoxyphenyl)methyl]-N-methyl(2-phenylpyridino[2,3-b]pyridin-4-yl)carboxamide | 6.34 |

TABLE 2a-continued

| Compound | Name | GC Retention Time (min) |
|---|---|---|
| 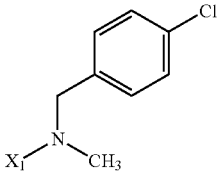 | N-[1-(4-chlorophenyl)methyl]-N-methyl(2-phenylpyridino[2,3-b]pyridin-4-yl)carboxamide | 6.36 |
| 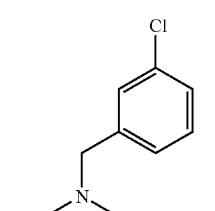 | N-[1-(3-chlorophenyl)methyl]-N-methyl(2-phenylpyridino[2,3-b]pyridin-4-yl)carboxamide | 6.32 |
| 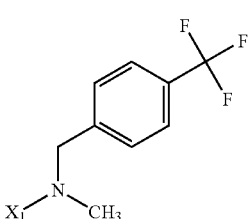 | N-[1-(4-trifluoromethylphenyl)methyl]-N-methyl(2-phenylpyridino[2,3-b]pyridin-4-yl)carboxamide | 5.92 |
| 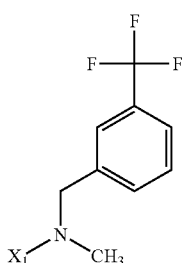 | N-[1-(3-trifluoromethylphenyl)methyl]-N-methyl(2-phenylpyridino[2,3-b]pyridin-4-yl)carboxamide | 5.9 |
| 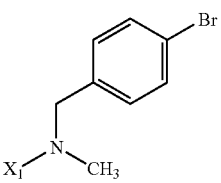 | N-[1-(4-bromophenyl)methyl]-N-methyl(2-phenylpyridino[2,3-b]pyridin-4-yl)carboxamide | 6.51 |
| 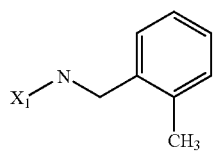 | N-[1-(2-methylphenyl)methyl](2-phenylpyridino[2,3-b]pyridin-4-yl)carboxamide | 6.53 |
| 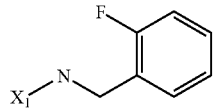 | N-[1-(2-fluorophenyl)methyl](2-phenylpyridino[2,3-b]pyridin-4-yl)carboxamide | 6.32 |

TABLE 2a-continued

| Compound | Name | GC Retention Time (min) |
|---|---|---|
| (2-methoxybenzyl)amine structure | N-[1-(2-methoxyphenyl)methyl](2-phenylpyridino[2,3-b]pyridin-4-yl)carboxamide | 6.62 |
| (2-chlorobenzyl)amine structure | N-[1-(2-chlorophenyl)methyl](2-phenylpyridino[2,3-b]pyridin-4-yl)carboxamide | 6.62 |
| (2-trifluoromethylbenzyl)amine structure | N-[1-(2-trifluoromethylphenyl)methyl](2-phenylpyridino[2,3-b]pyridin-4-yl)carboxamide | 6.19 |
| (2-methylphenethyl)amine structure | N-[1-(2-methylphenyl)ethyl](2-phenylpyridino[2,3-b]pyridin-4-yl)carboxamide | 6.67 |
| (2-fluorophenethyl)amine structure | N-[1-(2-fluorophenyl)ethyl](2-phenylpyridino[2,3-b]pyridin-4-yl)carboxamide | 6.47 |
| (2-methoxyphenethyl)amine structure | N-[1-(2-methoxyphenyl)ethyl](2-phenylpyridino[2,3-b]pyridin-4-yl)carboxamide | 6.74 |
| (2-chlorophenethyl)amine structure | N-[1-(2-chlorophenyl)ethyl](2-phenylpyridino[2,3-b]pyridin-4-yl)carboxamide | 6.8 |
| (2-trifluoromethylphenethyl)amine structure | N-[1-(2-trifluoromethylphenyl)ethyl](2-phenylpyridino[2,3-b]pyridin-4-yl)carboxamide | 6.41 |
| (2,4-dichlorophenethyl)amine structure | N-[1-(2,4-dichlorophenyl)ethyl](2-phenylpyridino[2,3-b]pyridin-4-yl)carboxamide | 7.15 |
| (4-methylbenzyl)amine structure | N-[1-(4-methylphenyl)methyl](2-phenylpyridino[2,3-b]pyridin-4-yl)carboxamide | 6.66 |

TABLE 2a-continued

| Compound | Name | GC Retention Time (min) |
|---|---|---|
| | N-[1-(3-methylphenyl)methyl](2-phenylpyridino[2,3-b]pyridin-4-yl)carboxamide | 6.63 |
| | N-[1-(4-fluorophenyl)methyl](2-phenylpyridino[2,3-b]pyridin-4-yl)carboxamide | 6.51 |
| | N-[1-(3-fluorophenyl)methyl](2-phenylpyridino[2,3-b]pyridin-4-yl)carboxamide | 6.5 |
| | N-[1-(4-methoxyphenyl)methyl](2-phenylpyridino[2,3-b]pyridin-4-yl)carboxamide | 6.97 |
| | N-[1-(3-methoxyphenyl)methyl](2-phenylpyridino[2,3-b]pyridin-4-yl)carboxamide | 6.89 |
| | N-[1-(4-chlorophenyl)methyl](2-phenylpyridino[2,3-b]pyridin-4-yl)carboxamide | 6.91 |
| | N-[1-(3-chlorophenyl)methyl](2-phenylpyridino[2,3-b]pyridin-4-yl)carboxamide | 6.9 |
| | N-[1-(4-trifluoromethylphenyl)methyl](2-phenylpyridino[2,3-b]pyridin-4-yl)carboxamide | 6.48 |
| | N-[1-(3-trifluoromethylphenyl)methyl](2-phenylpyridino[2,3-b]pyridin-4-yl)carboxamide | 6.44 |

TABLE 2a-continued

| Compound | Name | GC Retention Time (min) |
|---|---|---|
| 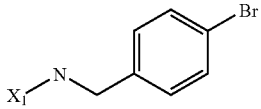 | N-[1-(4-bromophenyl)methyl](2-phenylpyridino[2,3-b]pyridin-4-yl)carboxamide | 7.17 |

TABLE 2b

| Compound | Name | GC Retention Time (min) |
|---|---|---|
| 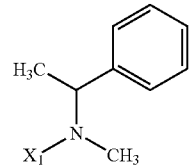 | N-[1-(phenyl)ethyl]-N-methyl(2-phenylpyridino[4,3-b]pyridin-4-yl)carboxamide | 6.14 |
| 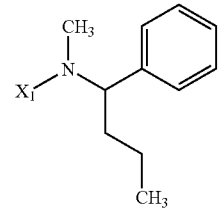 | N-[1-(phenyl)butyl]-N-methyl(2-phenylpyridino[4,3-b]pyridin-4-yl)carboxamide | 6.28 |
| 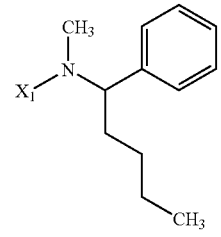 | N-[1-(phenyl)pentyl]-N-methyl(2-phenylpyridino[4,3-b]pyridin-4-yl)carboxamide | 6.38 |
| 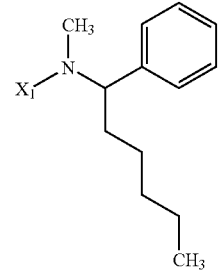 | N-[1-(phenyl)hexyl]-N-methyl(2-phenylpyridino[4,3-b]pyridin-4-yl)carboxamide | 6.51 |
| 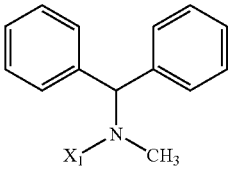 | N-[1-(diphenyl)methyl]-N-methyl(2-phenylpyridino[4,3-b]pyridin-4-yl)carboxamide | 6.81 |

TABLE 2b-continued

| Compound | Name | GC Retention Time (min) |
|---|---|---|
|  | N-[1-(1,2-diphenyl)ethyl]-N-methyl(2-phenylpyridino[4,3-b]pyridin-4-yl)carboxamide | 7.09 |
|  | N-[1-(1-phenyl-2-cyclohexyl)ethyl]-N-methyl(2-phenylpyridino[4,3-b]pyridin-4-yl)carboxamide | 6.95 |
|  | N-indanyl-N-methyl(2-phenylpyridino[4,3-b]pyridin-4-yl)carboxamide | 6.48 |
|  | N-[1-(phenyl)isobutyl]-N-methyl(2-phenylpyridino[4,3-b]pyridin-4-yl)carboxamide | 6.23 |
|  | N-[1-(phenyl)2-methylbutyl]-N-methyl(2-phenylpyridino[4,3-b]pyridin-4-yl)carboxamide | 6.28 |
|  | 1-isobutyl(2-1,2,3,4-tetrahydroisoquinolyl)(2-phenylpyridino[4,3-b]pyridin-4-yl)ketone | 6.66 |
|  | 1-(2-methylphenyl)(2-1,2,3,4-tetrahydroisoquinolyl)(2-phenylpyridino[4,3-b]pyridin-4-yl)ketone | 7.48 |

TABLE 2b-continued

| Compound | Name | GC Retention Time (min) |
|---|---|---|
| | 1-(2-chlorophenyl)(2-1,2,3,4-tetrahydroisoquinolyl)(2-phenylpyridino[4,3-b]pyridin-4-yl)ketone | 7.79 |
| | 1-methyl(2-1,2,3,4-tetrahydroisoquinolyl)(2-phenylpyridino[4,3-b]pyridin-4-yl)ketone | 6.46 |
| | 1-propyl(2-1,2,3,4-tetrahydroisoquinolyl)(2-phenylpyridino[4,3-b]pyridin-4-yl)ketone | 6.58 |
| | 1-butyl(2-1,2,3,4-tetrahydroisoquinolyl)(2-phenylpyridino[4,3-b]pyridin-4-yl)ketone | 6.67 |
| | 1-cyclopentyl(2-1,2,3,4-tetrahydroisoquinolyl)(2-phenylpyridino[4,3-b]pyridin-4-yl)ketone | 7.08 |
| | 1-pentyl(2-1,2,3,4-tetrahydroisoquinolyl)(2-phenylpyridino[4,3-b]pyridin-4-yl)ketone | 6.81 |
| | 1-benzyl(2-1,2,3,4-tetrahydroisoquinolyl)(2-phenylpyridino[4,3-b]pyridin-4-yl)ketone | 7.53 |

TABLE 2b-continued

| Compound | Name | GC Retention Time (min) |
|---|---|---|
| | 1-cyclohexylmethyl(2-1,2,3,4-tetrahydroisoquinolyl)(2-phenylpyridino[4,3-b]pyridin-4-yl)ketone | 7.39 |
| | 1-isopropyl(2-1,2,3,4-tetrahydroisoquinolyl)(2-phenylpyridino[4,3-b]pyridin-4-yl)ketone | 6.55 |
| | N-[1-(phenyl)octyl]-N-methyl(2-phenylpyridino[4,3-b]pyridin-4-yl)carboxamide | 6.55 |
| | 1-(2-methylbutyl)(2-1,2,3,4-tetrahydroisoquinolyl)(2-phenylpyridino[4,3-b]pyridin-4-yl)ketone | 6.51 |
| | N-[1,3-(diphenyl)propyl]-N-methyl(2-phenylpyridino[4,3-b]pyridin-4-yl)carboxamide | 6.98 |
| | N-[1,4-(diphenyl)butyl]-N-methyl(2-phenylpyridino[4,3-b]pyridin-4-yl)carboxamide | 7.18 |

TABLE 2b-continued

| Compound | Name | GC Retention Time (min) |
|---|---|---|
|  | N-benzyl-N-methyl(2-phenylpyridino[4,3-b]pyridin-4-yl)carboxamide | 5.88 |
|  | N-benzyl-N-ethyl(2-phenylpyridino[4,3-b]pyridin-4-yl)carboxamide | 5.9 |
|  | N-benzyl-N-isopropyl(2-phenylpyridino[4,3-b]pyridin-4-yl)carboxamide | 5.9 |
|  | N-benzyl-N-butyl(2-phenylpyridino[4,3-b]pyridin-4-yl)carboxamide | 6.06 |
|  | N-benzyl-N-isobutyl(2-phenylpyridino[4,3-b]pyridin-4-yl)carboxamide | 5.97 |
|  | N-benzyl-N-cyclopentyl(2-phenylpyridino[4,3-b]pyridin-4-yl)carboxamide | 6.36 |
|  | N-benzyl-N-pentyl(2-phenylpyridino[4,3-b]pyridin-4-yl)carboxamide | 6.17 |
|  | N-methyl(2-phenylpyridino[4,3-b]pyridin-4-yl)carboxamide | 5.25 |
|  | N-[1-(phenylcyclopentyl)methyl]-N-methyl(2-phenylpyridino[4,3-b]pyridin-4-yl)carboxamide | 6.64 |

TABLE 2b-continued

| Compound | Name | GC Retention Time (min) |
|---|---|---|
| | N-[1-(phenylcyclohexyl)methyl]-N-methyl(2-phenylpyridino[4,3-b]pyridin-4-yl)carboxamide | 6.79 |
| | N-[1-(1-phenyl-2cyclopentyl)ethyl]-N-methyl(2-phenylpyridino[4,3-b]pyridin-4-yl)carboxamide | 6.71 |
| | N-[1-(1,3-diphenyl)propyl]-N-methyl(2-phenylpyridino[4,3-b]pyridin-4-yl)carboxamide | 7.19 |
| | N-[1-(1,4-diphenyl)butyl]-N-methyl(2-phenylpyridino[4,3-b]pyridin-4-yl)carboxamide | 7.44 |
| | 1-phenyl(2-1,2,3,4-tetrahydroisoquinolyl)(2-phenylpyridino[4,3-b]pyridin-4-yl)ketone | 6.86 |
| | 1-cyclohexyl(2-1,2,3,4-tetrahydroisoquinolyl)(2-phenylpyridino[4,3-b]pyridin-4-yl)ketone | 6.87 |
| | 1-cyclopentylmethyl(2-1,2,3,4-tetrahydroisoquinolyl)(2-phenylpyridino[4,3-b]pyridin-4-yl)ketone | 6.76 |

TABLE 2b-continued

| Compound | Name | GC Retention Time (min) |
|---|---|---|
| | 1-hexyl(2-1,2,3,4-tetrahydroisoquinolyl)(2-phenylpyridino[4,3-b]pyridin-4-yl)ketone | 6.62 |
| | 1-(2-fluorophenyl)(2-1,2,3,4-tetrahydroisoquinolyl)(2-phenylpyridino[4,3-b]pyridin-4-yl)ketone | 6.84 |
| | 1-(3-methylphenyl)(2-1,2,3,4-tetrahydroisoquinolyl)(2-phenylpyridino[4,3-b]pyridin-4-yl)ketone | 7.29 |
| | 1-(4-methylphenyl)(2-1,2,3,4-tetrahydroisoquinolyl)(2-phenylpyridino[4,3-b]pyridin-4-yl)ketone | 7.43 |
| | 1-(4-fluorophenyl)(2-1,2,3,4-tetrahydroisoquinolyl)(2-phenylpyridino[4,3-b]pyridin-4-yl)ketone | 7.15 |
| | 1-cycloheptyl(2-1,2,3,4-tetrahydroisoquinolyl)(2-phenylpyridino[4,3-b]pyridin-4-yl)ketone | 7.54 |
| | 1-(3-chlorophenyl)(2-1,2,3,4-tetrahydroisoquinolyl)(2-phenylpyridino[4,3-b]pyridin-4-yl)ketone | 7.66 |

TABLE 2b-continued

| Compound | Name | GC Retention Time (min) |
|---|---|---|
| (4-chlorophenyl-tetrahydroisoquinoline with X₁ on N) | 1-(4-chlorophenyl)(2-1,2,3,4-tetrahydroisoquinolyl)(2-phenylpyridino[4,3-b]pyridin-4-yl)ketone | 7.77 |
| (6,7-dimethoxy-tetrahydroisoquinoline with X₁ on N) | 6,7-dimethoxy(2-1,2,3,4-tetrahydroisoquinolyl)(2-phenylpyridino[4,3-b]pyridin-4-yl)ketone | 7.23 |
| (6,7-dimethoxy-1-methyl-tetrahydroisoquinoline with X₁ on N) | 6,7-dimethoxy-1-methyl(2-1,2,3,4-tetrahydroisoquinolyl)(2-phenylpyridino[4,3-b]pyridin-4-yl)ketone | 7.11 |
| (6,7-dimethoxy-1-phenyl-tetrahydroisoquinoline with X₁ on N) | 6,7-dimethoxy-1-phenyl(2-1,2,3,4-tetrahydroisoquinolyl)(2-phenylpyridino[4,3-b]pyridin-4-yl)ketone | 8.35 |
| (6,7-dimethoxy-3-methyl-tetrahydroisoquinoline with X₁ on N) | 6,7-dimethoxy-3-methyl(2-1,2,3,4-tetrahydroisoquinolyl)(2-phenylpyridino[4,3-b]pyridin-4-yl)ketone | 7.1 |
| (6,7-dimethoxy-tetrahydroisoquinoline with ethanenitrile and X₁ on N) | 2-[6,7-dimethoxy-2-(2-1,2,3,4-tetrahydroisoquinolyl)(2-phenylpyridino[4,3-b]pyridin-4-yl)]ethanenitrile ketone | 7.85 |
| (N-[1-(4-bromophenyl)ethyl] with X₁ on N) | N-[1-(4-bromophenyl)ethyl](2-phenylpyridino[4,3-b]pyridin-4-yl)carboxamide | 6.95 |
| (N-[1-(4-methylphenyl)ethyl] with X₁ on N) | N-[1-(4-methylphenyl)ethyl](2-phenylpyridino[4,3-b]pyridin-4-yl)carboxamide | 6.48 |
| (N-[1-(3-methylphenyl)ethyl] with X₁ on N) | N-[1-(3-methylphenyl)ethyl](2-phenylpyridino[4,3-b]pyridin-4-yl)carboxamide | 6.47 |

TABLE 2b-continued

| Compound | Name | GC Retention Time (min) |
|---|---|---|
| (X₁-N-CH₂CH₂-C₆H₄-4-F structure) | N-[1-(4-fluorophenyl)ethyl](2-phenylpyridino[4,3-b]pyridin-4-yl)carboxamide | F |
| (X₁-N-CH₂CH₂-C₆H₄-3-F structure) | N-[1-(3-fluorophenyl)ethyl](2-phenylpyridino[4,3-b]pyridin-4-yl)carboxamide | 6.38 |
| (X₁-N-CH₂CH₂-C₆H₄-4-OCH₃ structure) | N-[1-(4-methoxyphenyl)ethyl](2-phenylpyridino[4,3-b]pyridin-4-yl)carboxamide | 6.74 |
| (3-methoxyphenyl-CH₂CH₂-N-X₁ structure) | N-[1-(3-methoxyphenyl)ethyl](2-phenylpyridino[4,3-b]pyridin-4-yl)carboxamide | 6.68 |
| (X₁-N-CH₂CH₂-C₆H₄-4-Cl structure) | N-[1-(4-chlorophenyl)ethyl](2-phenylpyridino[4,3-b]pyridin-4-yl)carboxamide | 6.74 |
| (X₁-N-CH₂CH₂-C₆H₄-3-Cl structure) | N-[1-(3-chlorophenyl)ethyl](2-phenylpyridino[4,3-b]pyridin-4-yl)carboxamide | 6.71 |
| (X₁-N-CH₂CH₂-C₆H₄-4-CF₃ structure) | N-[1-(4-trifluoromethylphenyl)ethyl](2-phenylpyridino[4,3-b]pyridin-4-yl)carboxamide | 6.34 |
| (X₁-N-CH₂CH₂-C₆H₄-3-CF₃ structure) | N-[1-(3-trifluoromethylphenyl)ethyl](2-phenylpyridino[4,3-b]pyridin-4-yl)carboxamide | 6.29 |
| (4-methylphenyl-CH₂-N(CH₃)-X₁ structure) | N-[1-(4-methylphenyl)methyl]-N-methyl(2-phenylpyridino[4,3-b]pyridin-4-yl)carboxamide | 5.93 |

TABLE 2b-continued

| Compound | Name | GC Retention Time (min) |
|---|---|---|
| (3-methylphenyl structure) | N-[1-(3-methylphenyl)methyl]-N-methyl(2-phenylpyridino[4,3-b]pyridin-4-yl)carboxamide | 5.88 |
| (4-fluorophenyl structure) | N-[1-(4-fluorophenyl)methyl]-N-methyl(2-phenylpyridino[4,3-b]pyridin-4-yl)carboxamide | 5.77 |
| (3-fluorophenyl structure) | N-[1-(3-fluorophenyl)methyl]-N-methyl(2-phenylpyridino[4,3-b]pyridin-4-yl)carboxamide | 5.76 |
| (4-methoxyphenyl structure) | N-[1-(4-methoxyphenyl)methyl]-N-methyl(2-phenylpyridino[4,3-b]pyridin-4-yl)carboxamide | 6.17 |
| (3-methoxyphenyl structure) | N-[1-(3-methoxyphenyl)methyl]-N-methyl(2-phenylpyridino[4,3-b]pyridin-4-yl)carboxamide | 6.1 |
| (4-chlorophenyl structure) | N-[1-(4-chlorophenyl)methyl]-N-methyl(2-phenylpyridino[4,3-b]pyridin-4-yl)carboxamide | 6.12 |
| (3-chlorophenyl structure) | N-[1-(3-chlorophenyl)methyl]-N-methyl(2-phenylpyridino[4,3-b]pyridin-4-yl)carboxamide | 6.07 |

TABLE 2b-continued

| Compound | Name | GC Retention Time (min) |
|---|---|---|
| (4-trifluoromethylbenzyl, N-methyl structure with X₁) | N-[1-(4-trifluoromethylphenyl)methyl]-N-methyl(2-phenylpyridino[4,3-b]pyridin-4-yl)carboxamide | 5.69 |
| (3-trifluoromethylbenzyl, N-methyl structure with X₁) | N-[1-(3-trifluoromethylphenyl)methyl]-N-methyl(2-phenylpyridino[4,3-b]pyridin-4-yl)carboxamide | 5.65 |
| (4-bromobenzyl, N-methyl structure with X₁) | N-[1-(4-bromophenyl)methyl]-N-methyl(2-phenylpyridino[4,3-b]pyridin-4-yl)carboxamide | 6.28 |
| (2-methylbenzyl structure with X₁) | N-[1-(2-methylphenyl)methyl](2-phenylpyridino[4,3-b]pyridin-4-yl)carboxamide | 6.28 |
| (2-fluorobenzyl structure with X₁) | N-[1-(2-fluorophenyl)methyl](2-phenylpyridino[4,3-b]pyridin-4-yl)carboxamide | 6.08 |
| (2-methoxybenzyl structure with X₁) | N-[1-(2-methoxyphenyl)methyl](2-phenylpyridino[4,3-b]pyridin-4-yl)carboxamide | 6.4 |
| (2-chlorobenzyl structure with X₁) | N-[1-(2-chlorophenyl)methyl](2-phenylpyridino[4,3-b]pyridin-4-yl)carboxamide | 6.37 |
| (2-trifluoromethylbenzyl structure with X₁) | N-[1-(2-trifluoromethylphenyl)methyl](2-phenylpyridino[4,3-b]pyridin-4-yl)carboxamide | 5.92 |

TABLE 2b-continued

| Compound | Name | GC Retention Time (min) |
|---|---|---|
| X₁–N–CH₂CH₂–(2-methylphenyl) | N-[1-(2-methylphenyl)ethyl](2-phenylpyridino[4,3-b]pyridin-4-yl)carboxamide | 6.42 |
| X₁–N–CH₂CH₂–(2-fluorophenyl) | N-[1-(2-fluorophenyl)ethyl](2-phenylpyridino[4,3-b]pyridin-4-yl)carboxamide | 6.24 |
| X₁–N–CH₂CH₂–(2-methoxyphenyl) | N-[1-(2-methoxyphenyl)ethyl](2-phenylpyridino[4,3-b]pyridin-4-yl)carboxamide | 6.48 |
| X₁–N–CH₂CH₂–(2-chlorophenyl) | N-[1-(2-chlorophenyl)ethyl](2-phenylpyridino[4,3-b]pyridin-4-yl)carboxamide | 6.53 |
| X₁–N–CH₂CH₂–(2-trifluoromethylphenyl) | N-[1-(2-trifluoromethylphenyl)ethyl](2-phenylpyridino[4,3-b]pyridin-4-yl)carboxamide | 6.15 |
| X₁–N–CH₂CH₂–(2,4-dichlorophenyl) | N-[1-(2,4-dichlorophenyl)ethyl](2-phenylpyridino[4,3-b]pyridin-4-yl)carboxamide | 6.84 |
| X₁–N–CH₂–(4-methylphenyl) | N-[1-(4-methylphenyl)methyl](2-phenylpyridino[4,3-b]pyridin-4-yl)carboxamide | 6.42 |
| X₁–N–CH₂–(3-methylphenyl) | N-[1-(3-methylphenyl)methyl](2-phenylpyridino[4,3-b]pyridin-4-yl)carboxamide | 6.38 |
| X₁–N–CH₂–(4-fluorophenyl) | N-[1-(4-fluorophenyl)methyl](2-phenylpyridino[4,3-b]pyridin-4-yl)carboxamide | 6.26 |

TABLE 2b-continued

| Compound | Name | GC Retention Time (min) |
|---|---|---|
| (3-fluorobenzyl structure) | N-[1-(3-fluorophenyl)methyl](2-phenylpyridino[4,3-b]pyridin-4-yl)carboxamide | 6.25 |
| (4-methoxybenzyl structure) | N-[1-(4-methoxyphenyl)methyl](2-phenylpyridino[4,3-b]pyridin-4-yl)carboxamide | 6.67 |
| (3-methoxybenzyl structure) | N-[1-(3-methoxyphenyl)methyl](2-phenylpyridino[4,3-b]pyridin-4-yl)carboxamide | 6.61 |
| (4-chlorobenzyl structure) | N-[1-(4-chlorophenyl)methyl](2-phenylpyridino[4,3-b]pyridin-4-yl)carboxamide | 6.63 |
| (3-chlorobenzyl structure) | N-[1-(3-chlorophenyl)methyl](2-phenylpyridino[4,3-b]pyridin-4-yl)carboxamide | 6.6 |
| (4-trifluoromethylbenzyl structure) | N-[1-(4-trifluoromethylphenyl)methyl](2-phenylpyridino[4,3-b]pyridin-4-yl)carboxamide | 6.21 |
| (3-trifluoromethylbenzyl structure) | N-[1-(3-trifluoromethylphenyl)methyl](2-phenylpyridino[4,3-b]pyridin-4-yl)carboxamide | 6.16 |
| (4-bromobenzyl structure) | N-[1-(4-bromophenyl)methyl](2-phenylpyridino[4,3-b]pyridin-4-yl)carboxamide | 6.83 |

The compounds in Table 2c may be prepared according to Scheme 2. For example, the appropriate acid is treated with diamine in the presence of BOP coupling reagent and base to form an aminoamide derivative. In a subsequent step, this material is treated with carbon tetrachloride in the presence of triphenylphosphine and triethylamine at room temperature to reflux over 2–18 h.

TABLE 2c

| Structure | Compound Name |
|---|---|
| 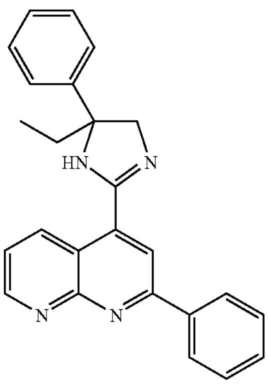 | 4-ethyl-4-phenyl-2-(2-phenylpyridino[2,3-b]pyridin-4-yl)imidazoline |
| 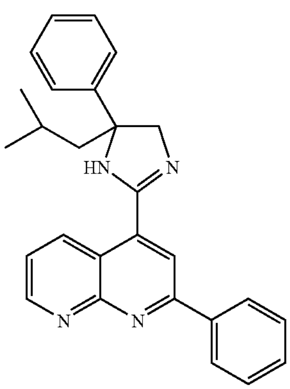 | 4-isobutyl-4-phenyl-2-(2-phenylpyridino[2,3-b]pyridin-4-yl)imidazoline |
| 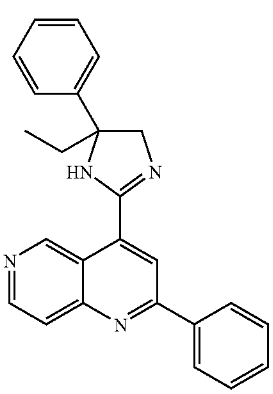 | 4-ethyl-4-phenyl-2-(2-phenylpyridino[4,3-b]pyridin-4-yl)imidazoline |
|  | 4-isobutyl-4-phenyl-2-(2-phenylpyridino[4,3-b]pyridin-4-yl)imidazoline |

EXAMPLE IX

The following assay is a standard assay of NK3 receptor binding, which is used to determine the NK-3 receptor binding affinity of compounds.

Assays are performed as described in Krause et al (Proc. Natl. Acad. Sci. USA 94: 310–315, 1997). The NK-3 receptor complementary DNA was cloned from human hypothalamic RNA using standard procedures. The receptor cDNA was inserted into the expression vector $pM^2$ to transfect the mammalian Chinese hamster ovary cell line, and a stably expressing clonal cell line was isolated, characterized and used for the current experiments. Cells are grown in minimal essential medium alpha containing 10% fetal bovine serum and 0.8 mg G418 per ml. Cells were liberated from cell culture plates with No-zyme (PBS base, JRH Biosciences), and harvested by low speed centrifugation. The cell pellet was homogenized in TBS (0.05 m TrisHCl, 120 mM NaCl, pH 7.4) with a Polytron homogenizer at setting 5 for 20 seconds, and total cellular membranes were isolated by centrifugation at 47,500×g for 10 minutes. The membrane pellet was resuspended by homogenization with the Polytron as above, and the membranes were isolated by centrifugation at 47,500×g for 10 minutes. This final membrane pellet was resuspended in TBS at a protein concentration of 350 μg/ml.

Receptor binding assays contain a total volume of 200 μl containing 50 μg membrane protein, 0.15 nM $^{125}$I-methylPhe$^7$-neurokinin B, drug or blocker in TBS containing 1.0 mg/ml bovine serum albumen, 0.2 mg/ml bacitracin, 20 ug/ml leupeptin and 20 μg/ml chymostatin. Incubations are carried out for 2 hours at 4° C., and the membrane proteins are harvested by passing the incubation mixture by rapid filtration over presoaked GF/B filters to separate bound from free ligand. The filters are presoaked in TBS containing 2% BSA and 0.1% Tween 20. After filtration of the incubation mixture, filters are rinsed 4 times with ice-cold TBS containing 0.01% sodium dodecyl sulfate and counted in a β-plate scintillation counter. One μM methylPhe$^7$-neurokinin B is added to some tubes to determine nonspecific binding. Data are collected in duplicate determinations, averaged, and the percent inhibition of total specific binding is calculated. The total specific binding is the total binding minus the nonspecific binding. In many cases, the concentration of unlabeled drug is varied and total displacement curves of binding is carried out. Data are converted to a form for the calculation of $IC_{50}$ and Hill coefficient (nH). Data for compounds of this invention are listed in Table 3.

TABLE 3

| Compound Number[1] | $IC_{50}$ (μM) |
|---|---|
| 1 | 0.05 |
| 2 | 0.08 |
| 3 | 0.10 |

[1]Compound numbers correspond to the compounds presented in Table 1 above.

EXAMPLE X

Preparation of Radiolabeled Probe Compounds of the Invention

The compounds of the invention are prepared as radiolabeled probes by carrying out their synthesis using precursors comprising at least one atom that is a radioisotope. The radioisotope is preferably selected from of at least one of carbon (preferably $^{14}C$), hydrogen (preferably $^{3}H$), sulfur (preferably $^{35}S$), or iodine (preferably $^{125}I$). A commercial laboratory specializing in custom synthesis of radiolabeled probe compounds conveniently carries out synthesis of such radiolabeled probes. Such laboratories include Amersham Corporation, Arlington Heights, Ill.; Cambridge Isotope Laboratories, Inc. Andover, Mass.; SRI International, Menlo Park, Calif.; Wizard Laboratories, West Sacramento, Calif.; ChemSyn Laboratories, Lexena, Kans.; American Radiolabeled Chemicals, Inc., St. Louis, Mo.; and Moravek Biochemicals Inc., Brea, Calif.

Tritium-labeled probe compounds are also conveniently prepared catalytically via platinum-catalyzed exchange in tritiated acetic acid, acid-catalyzed exchange in tritiated trifluoroacetic acid, or heterogeneous-catalyzed exchange with tritium gas. Such preparations are also conveniently carried out as a custom radiolabeling by any of the suppliers listed in the preceding paragraph using the compound of the invention as substrate. In addition, certain precursors may be subjected to tritium-halogen exchange with tritium gas, tritium gas reduction of unsaturated bonds, or reduction using sodium borotritide, as appropriate.

EXAMPLE XI

Use of Compounds of the Invention as Probes for Detecting NK-3 Receptors in Cultured Cells and Tissue Samples (e.g., Tissue Sections)

Receptor autoradiography (receptor mapping) of NK-3 receptors in cultured cells or tissue samples is carried out in vitro as described by Kuhar in sections 8.1.1 to 8.1.9 of Current Protocols in Pharmacology (1998) John Wiley & Sons, New York, using radiolabeled compounds of the invention prepared as described in the preceding Example.

The invention and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the spirit or scope of the present invention as set forth in the claims. To particularly point out and distinctly claim the subject matter regarded as invention, the following claims conclude this specification.

What is claimed is:
1. A compound of the formula:

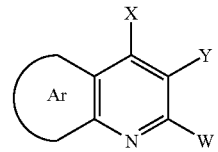

or pharmaceutically acceptable non-toxic salts or pharmaceutically acceptable solvates thereof wherein:

Y is
  hydrogen, straight or branched chain lower alkyl having 1–6 carbon atoms,
  halogen, amino, hydroxyl, or lower alkoxy having 1–6 carbon atoms; or Y is
  straight or branched chain lower alkyl having 1–6 carbon atoms or lower alkoxy having 1–6 carbon atoms each of which is substituted on the alkyl chain with an amino or mono or dialkylamino group where each alkyl is independently lower alkyl;

W is
  phenyl, thienyl, or pyridyl, each of which may be mono or disubstituted with halogen, cyano, trifluoromethyl, trifluoromethoxy, hydroxy, straight or branched chain lower alkyl having 1–6 carbon atoms, straight or branched chain lower alkoxy having 1–6 carbon atoms, amino, or mono or dialkylamino where each alkyl is straight or branched chain lower alkyl having 1–6 carbon atoms;

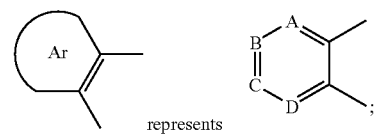

wherein:
  A represents C—$R_1$;
  B represents C—$R_2$;
  C represents C—$R_3$;
D represents nitrogen;
$R_1$ through $R_3$ are the same or different and represent
  hydrogen, halogen, cyano, trifluoromethyl, trifluoromethoxy, hydroxy, straight or branched chain lower alkyl having 1–6 carbon atoms, amino, mono or dialkylamino where each alkyl is straight or branched chain lower alkyl having 1–6 carbon atoms, or straight or branched chain lower alkoxy having 1–6 carbon atoms:
X is dihydroimidazolyl, —CONR$_6$R$_7$, or —NR$_7$COR$_6$, where
  $R_6$ is ($C_3$–$C_6$)cycloalkyl($C_1$–$C_6$)alkyl, alkyl substituted with optionally substituted phenyl, or cycloalkyl fused to phenyl;
  $R_7$ represents hydrogen or straight or branched chain lower alkyl having 1–6 carbon atoms; or R₆ and R₇ together form a 6-membered ring fused to a benzene to form a tetrahydroisoquinoline group.

2. A compound according to claim 1, which is N—((S)-1-phenyl-1-propyl) (2-phenylpyridino[2,3-b]pyridin-4-yl) carboxamide.

3. A compound according to claim 1, which is N—((S)-1-phenyl-1-propyl)(2-phenylpyridino[2,3-b]pyridin-4-yl) carboxamide.

4. A compound according to claim 1, which is N-(Diphenylmethyl)N-methyl(2-phenylpyridino[2,3-b]pyridin-4-yl) carboxamide.

5. A compound according to claim 1, which is selected from the group consisting of
N-[1-(phenyl)ethyl]-N-methyl(2-phenylpyridino[2,3-b]pyridin-4-yl)carboxamide;
N-[1-(phenyl)butyl]-N-methyl (2-phenylpyridino[2,3-b]pyridin-4-yl) carboxamide;
N-[1-(phenyl)pentyl]-N-methyl(2-phenylpyridino[2,3-b]pyridin-4-yl)carboxamide;
N-[1-(phenyl)hexyl]-N-methyl(2-phenylpyridino[2,3-b]pyridin-4-yl)carboxamide;
N-[1-(diphenyl)methyl]-N-methyl(2-phenylpyridino[2,3-b]pyridin-4-yl)carboxamide;
N-[1-(1,2-diphenyl) ethyl]-N-methyl (2-phenylpyridino[2,3-b]pyridin-4-yl)carboxamide;
N-[1-(1-phenyl-2-cyclohexyl)ethyl]-N-methyl(2-phenylpyridino[2,3-b]pyridin-4-yl)carboxamide;
N-indanyl-N-methyl(2-phenylpyridino[2,3-b]pyridin-4-yl) carboxamide;
N-[1-(phenyl)isobutyl]-N-methyl(2-phenylpyridino[2,3-b]pyridin-4-yl)carboxamide; and
N-[1-(phenyl)2-methylbutyl]-N-methyl (2-phenylpyridino[2,3-b]pyridin-4-yl)carboxamide.

6. A compound according to claim 1, which is selected from the group consisting of
1-isobutyl(2-1,2,3,4-tetrahydroisoquinolyl)(2-phenylpyridino[2,3-b]pyridin-4-yl)ketone;
1-(2-methylphenyl)(2-1,2,3,4-tetrahydroisoquinolyl)(2-phenylpyridino[2,3-b]pyridin-4-yl) ketone;
1-(2-chlorophenyl)(2-1,2,3,4-tetrahydroisoquinolyl)(2-phenylpyridino[2,3-b]pyridin-4-yl)ketone;
1-methyl(2-1,2,3,4-tetrahydroisoquinolyl)(2-phenylpyridino[2,3-b]pyridin-4-yl) ketone;
1-propyl(2-1,2,3,4-tetrahydroisoquinolyl)(2-phenylpyridino[2,3-b]pyridin-4-yl) ketone;
1-butyl(2-1,2,3,4-tetrahydroisoquinolyl)(2-phenylpyridino[2,3-b]pyridin-4-yl) ketone;
1-cyclopentyl(2-1,2,3,4-tetrahydroisoquinolyl)(2-phenylpyridino[2,3-b]pyridin-4-yl) ketone;
1-pentyl(2-1,2,3,4-tetrahydroisoquinolyl)(2-phenylpyridino[2,3-b]pyridin-4-yl) ketone;
1-benzyl(2-1,2,3,4-tetrahydroisoquinolyl)(2-phenylpyridino[2,3-b]pyridin-4-yl) ketone;
1-cyclohexylmethyl(2-1,2,3,4-tetrahydroisoquinolyl)(2-phenylpyridino[2,3-b]pyridin-4-yl) ketone; and
1-isopropyl(2-1,2,3,4-tetrahydroisoquinolyl)(2-phenylpyridino[2,3-b]pyridin-4-yl) ketone.

7. A compound according to claim 1, which is selected from the group consisting of
N-[1-(phenyl) octyl]-N-methyl(2-phenylpyridino[2,3-b]pyridin-4-yl)carboxamide;
1-(2-methylbutyl)(2-1,2,3,4-tetrahydroisoquinolyl)(2-phenylpyridino[2,3-b]pyridin-4-yl) ketone;
N-[1,3-(diphenyl)propyl]-N-methyl(2-phenylpyridino[2,3-b]pyridin-4-yl)carboxamide;
N-[1,4-(diphenyl)butyl]-N-methyl(2-phenylpyridino[2,3-b]pyridin-4-yl)carboxamide;
N-benzyl-N-methyl(2-phenylpyridino[2,3-b]pyridin-4-yl)carboxamide;
N-benzyl-N-ethyl(2-phenylpyridino[2,3-b]pyridin-4-yl)carboxamide;
N-benzyl-N-isopropyl(2-phenylpyridino[2,3-b]pyridin-4-yl)carboxamide;
N-benzyl-N-butyl(2-phenylpyridino[2,3-b]pyridin-4-yl)carboxamide;
N-benzyl-N-isobutyl(2-phenylpyridino[2,3-b]pyridin-4-yl)carboxamide;
N-benzyl-N-cyclopentyl(2-phenylpyridino[2,3-b]pyridin-4-yl)carboxamide;
N-benzyl-N-pentyl(2-phenylpyridino[2,3-b]pyridin-4-yl)carboxamide; and
N-benzyl-N-cyclohexyl(2-phenylpyridino[2,3-b]pyridin-4-yl)carboxamide.

8. A compound according to claim 1, which is selected from the group consisting of
N,N-dibenzyl(2-phenylpyridino[2,3-b]pyridin-4-yl)carboxamide;
N-benzyl-N-1-methylpropyl(2-phenylpyridino[2,3-b]pyridin-4-yl)carboxamide;
N-benzyl-N-1-methylbutyl(2-phenylpyridino[2,3-b]pyridin-4-yl)carboxamide;
N-benzyl-N-4-methylbutyl (2-phenylpyridino[2,3-b]pyridin-4-yl)carboxamide;
N-benzyl-N-cyclopentylmethyl(2-phenylpyridino[2,3-b]pyridin-4-yl)carboxamide;
N-benzyl-N-hexyll (2-phenylpyridino[2,3-b]pyridin-4-yl)carboxamide;
N-benzyl-N-cyclohexylmethyl(2-phenylpyridino[2,3-b]pyridin-4-yl)carboxamide;
N-benzyl-N-heptyl(2-phenylpyridino[2,3-b]pyridin-4-yl)carboxamide;
N-methyl(2-phenylpyridino[2,3-b]pyridin-4-yl)carboxamide; and
N-[1-(phenylcyclopentyl)methyl]-N-methyl(2-phenylpyridino[2,3-b]pyridin-4-yl)carboxamide.

9. A compound according to claim 1, which is selected from the group consisting of
N-[1-(phenylcyclohexyl)methyl]-N-methyl(2-phenylpyridino[2,3-b]pyridin-4-yl)carboxamide;
N-[1-(1-phenyl-2cyclopentyl)ethyl]-N-methyl(2-phenylpyridino[2,3-b]pyridin-4-yl)carboxamide;
N-[1-(1,3-diphenyl) propyl]-N-methyl (2-phenylpyridino[2,3-b]pyridin-4-yl)carboxamide;
N-[1-(1,4-diphenyl)butyl]-N-methyl (2-phenylpyridino[2,3-]pyridin-4-yl)carboxamide;
1-phenyl (2-1,2,3,4-tetrahydroisoquinolyl)(2-phenylpyridino[2,3-b]pyridin-4-yl) ketone;
1-cyclohexyl(2-1,2,3,4-tetrahydroisoquinolyl)(2-phenylpyridino[2,3-b]pyridin-4-yl) ketone;
1-cyclopentylmethyl(2-1,2,3,4-tetrahydroisoquinolyl)(2-phenylpyridino[2,3-b]pyridih-4-yl) ketone;
1-hexyl(2-1,2,3,4-tetrahydroisoquinolyl)(2-phenylpyridino[2,3-b]pyridin-4-yl) ketone;
1-(2-fluorophenyl)(2-1,2,3,4-tetrahydroisoquinolyl)(2-phenylpyridino[2,3-b]pyridin-4-yl) ketone; and
1-(2-trifluoromethylphenyl)(2-1,2,3,4-tetrahydroisoquinolyl)(2-phenylpyridino[2,3-b]pyridin-4-yl) ketone.

10. A compound according to claim 1, which is selected from the group consisting of
1-(3-methylphenyl)(2-1,2,3,4-tetrahydroisoquinolyl)(2-phenylpyridino[2,3-b]pyridin-4-yl) ketone;
1-(4-methylphenyl)(2-1,2,3,4-tetrahydroisoquinolyl)(2-phenylpyridino[2,3-b]pyridin-4-yl) ketone;

1-(4-fluorophenyl)(2-1,2,3,4-tetrahydroisoquinolyl)(2-phenylpyridino[2,3-b]pyridin-4-yl) ketone;
1-cycloheptyl(2-1,2,3,4-tetrahydroisoquinolyl)(2-phenylpyridino[2,3-b]pyridin-4-yl) ketone;
1-(3-chlorophenyl)(2-1,2,3,4-tetrahydroisoquinolyl)(2-phenylpyridino[2,3-b]pyridin-4-yl) ketone;
1-(4-chlorophenyl)(2-1,2,3,4-tetrahydroisoquinolyl)(2-phenylpyridino[2,3-b]pyridin-4-yl) ketone;
6,7-dimethoxy(2-1,2,3,4-tetrahydroisoquinolyl)(2-phenylpyridino[2,3-b]pyridin-4-yl) ketone;
6,7-dimethoxy-1-methyl(2-1,2,3,4-tetrahydroisoquinolyl)(2-phenylpyridino[2,3-b]pyridin-4-yl) ketone;
6,7-dimethoxy-1-phenyl(2-1,2,3,4-tetrahydroisoquinolyl)(2-phenylpyridino[2,3-b]pyridin-4-yl) ketone; and
6,7-dimethoxy-3-methyl(2-1,2,3,4-tetrahydroisoquinolyl)(2-phenylpyridino[2,3-b]pyridin-4-yl) ketone.

11. A compound according to claim 1, which is selected from the group consisting of
2-[6,7-dimethoxy-2-(2-1,2,3,4-tetrahydroisoquinolyl)(2-phenylpyridino[2,3-b]pyridin-4-yl)]ethanenitrile ketone;
N-[1-(4-bromophenyl)ethyl](2-phenylpyridino[2,3-b]pyridin-4-yl)carboxamide;
N-[1-(4-methylphenyl)ethyl](2-phenylpyridino[2,3-b]pyridin-4-yl)carboxamide;
N-[1-(3-methylphenyl)ethyl](2-phenylpyridino[2,3-b]pyridin-4-yl)carboxamide;
N-[1-(4-fluorophenyl)ethyl](2-phenylpyridino[2,3-b]pyridin-4-yl)carboxamide;
N-[1-(3-fluorophenyl)ethyl](2-phenylpyridino[2,3-b]pyridin-4-yl)carboxamide;
N-[1-(4-methoxyphenyl) ethyl](2-phenylpyridino[2,3-b]pyridin-4-yl)carboxamide;
N-[1-(3-methoxyphenyl) ethyl](2-phenylpyridino[2,3-b]pyridin-4-yl)carboxamide;
N-[1-(4-chlorophenyl)ethyl](2-phenylpyridino[2,3-b]pyridin-4-yl)carboxamide;
N-[1-(3-chlorophenyl)ethyl](2-phenylpyridino[2,3-b]pyridin-4-yl)carboxamide; and
N-[1-(4-trifluoromethylphenyl)ethyl](2-phenylpyridino[2,3-b]pyridin-4-yl)carboxamide.

12. A compound according to claim 1, which is selected from the group consisting of
N-[1-(3-trifluoromethylphenyl)ethyl](2-phenylpyridino[2,3-b]pyridin-4-yl)carboxamide;
N-[1-(4-methylphenyl)methyl]-N-methyl(2-phenylpyridino[2,3-b]pyridin-4-yl)carboxamide;
N-[1-(3-methylphenyl)methyl]-N-methyl(2-phenylpyridino[2,3-b]pyridin-4-yl)carboxamide;
N-[1-(4-fluorophenyl)methyl]-N-methyl(2-phenylpyridino[2,3-]pyridin-4-yl)carboxamide;
N-[1-(3-fluorophenyl) methyl]-N-methyl(2-phenylpyridino[2,3-b]pyridin-4-yl)carboxamide;
N-[1-(4-methoxyphenyl)methyl]-N-methyl(2-phenylpyridino[2,3-b]pyridin-4-yl)carboxamide;
N-[1-(3-methoxyphenyl)methyl]-N-methyl(2-phenylpyridino[2,3-b]pyridin-4-yl)carboxamide;
N-[1-(4-chlorophenyl) methyl]-N-methyl(2-phenylpyridino[2,3-b]pyridin-4-yl)carboxamide; and
N-[1-(3-chlorophenyl)methyl]-N-methyl(2-phenylpyridino[2,3-b]pyridin-4-yl)carboxamide.

13. A compound according to claim 1, which is selected from the group consisting of
N-[1-(4-trifluoromethylphenyl)methyl]-N-methyl(2-phenylpyridino[2,3-b]pyridin-4-yl)carboxamide;
N-[1-(3-trifluoromethylphenyl)methyl]-N-methyl(2-phenylpyridino[2,3-b]pyridin-4-yl)carboxamide;
N-[1-(4-bromophenyl)methyl]-N-methyl (2-phenylpyridino[2,3-b]pyridin-4-yl)carboxamide;
N-[1-(2-methylphenyl)methyl](2-phenylpyridino[2,3-b]pyridin-4-yl)carboxamide;
N-[1-(2-fluorophenyl)methyl](2-phenylpyridino[2,3-b]pyridin-4-yl)carboxamide;
N-[1-(2-methoxyphenyl)methyl](2-phenylpyridino[2,3-b]pyridin-4-yl)carboxamide;
N-[1-(2-chlorophenyl)methyl](2-phenylpyridino[2,3-b]pyridin-4-yl)carboxamide;
N-[1-(2-trifluoromethylphenyl)methyl](2-phenylpyridino[2,3-b]pyridin-4-yl)carboxamide;
N-[1-(2-methylphenyl) ethyl](2-phenylpyridino[2,3-b]pyridin-4-yl)carboxamide; and
N-[1-(2-fluorophenyl)ethyl](2-phenylpyridino[2,3-b]pyridin-4-yl)carboxamide.

14. A compound according to claim 1, which is selected from the group consisting of
N-[1-(2-methoxyphenyl)ethyl](2-phenylpyridino[2,3-b]pyridin-4-yl)carboxamide;
N-[1-(2-chlorophenyl) ethyl](2-phenylpyridino[2,3-b]pyridin-4-yl)carboxamide;
N-[1-(2-trifluoromethylphenyl)ethyl](2-phenylpyridino[2,3-b]pyridin-4-yl)carboxamide;
N-[1-(2,4-dichlorophenyl)ethyl](2-phenylpyridino[2,3-b]pyridin-4-yl)carboxamide;
N-[1-(4-methylphenyl)methyl](2-phenylpyridino[2,3-b]pyridin-4-yl)carboxamide;
N-[1-(3-methylphenyl)methyl](2-phenylpyridino[2,3-b]pyridin-4-yl)carboxamide;
N-[1-(4-fluorophenyl)methyl](2-phenylpyridino[2,3-b]pyridin-4-yl)carboxamide;
N-[1-(3-fluorophenyl)methyl](2-phenylpyridino[2,3-b]pyridin-4-yl)carboxamide;
N-[1-(4-methoxyphenyl)methyl](2-phenylpyridino[2,3-b]pyridin-4-yl)carboxamide; and
N-[1-(3-methoxyphenyl)methyl](2-phenylpyridino[2,3-b]pyridin-4-yl)carboxamide.

15. A compound according to claim 1, which is selected from a group consisting of
N-[1-(4-chlorophenyl)methyl](2-phenylpyridino[2,3-b]pyridin-4-yl)carboxamide;
N-[1-(3-chlorophenyl)methyl](2-phenylpyridino[2,3-b]pyridin-4-yl)carboxamide;
N-[1-(4-trifluoromethylphenyl)methyl](2-phenylpyridino[2,3-b]pyridin-4-yl)carboxamide;
N-[1-(3-trifluoromethylphenyl)methyl](2-phenylpyridino[2,3-b]pyridin-4-yl)carboxamide; and
N-[1-(4-bromophenyl)methyl](2-phenylpyridino[2,3-b]pyridin-4-yl)carboxamide.

16. A compound according to claim 1 which is selected from the group consisting of:
4-ethyl-4-phenyl-2-(2-phenylpyridino[2,3-b]pyridin-4-yl) imidazoline; and
4-isobutyl-4-phenyl-2-(2-phenylpyridino[2,3-b]pyridin-4-yl) imidazoline.

17. A pharmaceutical composition comprising a compound according to claim 1 combined with at least one pharmaceutically acceptable carrier or excipient.

18. A method for the treatment of schizophrenia, said method comprising administering to a patient in need of such treatment an effective amount of a compound of claim 1.

19. A packaged pharmaceutical composition comprising the pharmaceutical composition of claim 17 in a container and instructions for using the composition to treat a patient suffering from schizophrenia.

* * * * *